(12) United States Patent
Lasker et al.

(10) Patent No.: US 7,463,362 B2
(45) Date of Patent: Dec. 9, 2008

(54) DIGITAL SIGNAL PROCESSOR-BASED DETECTION SYSTEM, METHOD, AND APPARATUS FOR OPTICAL TOMOGRAPHY

(75) Inventors: Joseph M. Lasker, Brooklyn, NY (US); Andreas Hielscher, Brooklyn, NY (US); James M. Masciotti, Hartsdale, NY (US); Christoph H. Schmitz, Brooklyn, NY (US); Mathew Schoenecker, Berkeley, CA (US)

(73) Assignees: The Trustees of Columbia University in the City of New York, New York, NY (US); The Research Foundation of State University of New York, Albany, NY (US)

(*) Notice: Subject to any disclaimer, the term of this patent is extended or adjusted under 35 U.S.C. 154(b) by 406 days.

(21) Appl. No.: 11/106,348

(22) Filed: Apr. 13, 2005

(65) Prior Publication Data

US 2005/0243322 A1 Nov. 3, 2005

Related U.S. Application Data

(60) Provisional application No. 60/561,989, filed on Apr. 13, 2004.

(51) Int. Cl.
*G01B 11/02* (2006.01)
*G01B 9/02* (2006.01)

(52) U.S. Cl. .................................. 356/497; 356/479
(58) Field of Classification Search ................ 356/479, 356/497
See application file for complete search history.

(56) References Cited

U.S. PATENT DOCUMENTS

| | | | |
|---|---|---|---|
| 4,807,146 A | 2/1989 | Goodrich et al. | |
| 4,970,637 A * | 11/1990 | Sato | 708/207 |
| 5,010,455 A | 4/1991 | Luallin et al. | |
| 5,137,355 A | 8/1992 | Barbour et al. | |
| 5,220,589 A * | 6/1993 | Gard | 378/19 |
| 5,528,365 A | 6/1996 | Gonatas | |
| 5,746,211 A | 5/1998 | Leigh et al. | |
| 6,011,401 A | 1/2000 | Henry et al. | |
| 6,549,284 B1 * | 4/2003 | Boas et al. | 356/446 |
| 6,795,195 B1 * | 9/2004 | Barbour et al. | 356/446 |
| 6,816,102 B2 * | 11/2004 | Pavicic | 341/155 |
| 2004/0239946 A1 * | 12/2004 | Kane et al. | 356/497 |
| 2008/0154126 A1 * | 6/2008 | Culver et al. | 600/426 |

OTHER PUBLICATIONS

Ducros et al. "Primage retina imaging with polarization-sensitive optical coherence tomography" Dec. 2001, J. Opt. Soc. Am. A. vol. 18, No. 12, pp. 2945-2956.*

* cited by examiner

*Primary Examiner*—Patrick J Connolly
(74) *Attorney, Agent, or Firm*—Wilmer Cutler Pickering Hale and Dorr LLP

(57) ABSTRACT

The present invention provides systems, methods and apparatuses that perform digital detection for use in optical tomography. Methods and systems are provided in which digital lock-in detection is performed using an algorithm that employs a phase-independent quadrature technique. Methods and systems are provided in which a unique manipulation of an ordinary averaging filter optimized for sources discrimination and the consequent sampling constraints is presented as a novel filtering scheme for the lock-in detection. Systems and apparatuses are provided which include a digital signal processor which performs digital lock-in detection and an integrated complex programmable logic device for timing control. Apparatuses are provided which include an instrument having an integrated digital signal processor for performing digital processing and detection for use in optical tomography.

51 Claims, 16 Drawing Sheets

New Digital System

Typical Analog System

New Digital System

Instrument Layout

Anti-Aliasing Filter

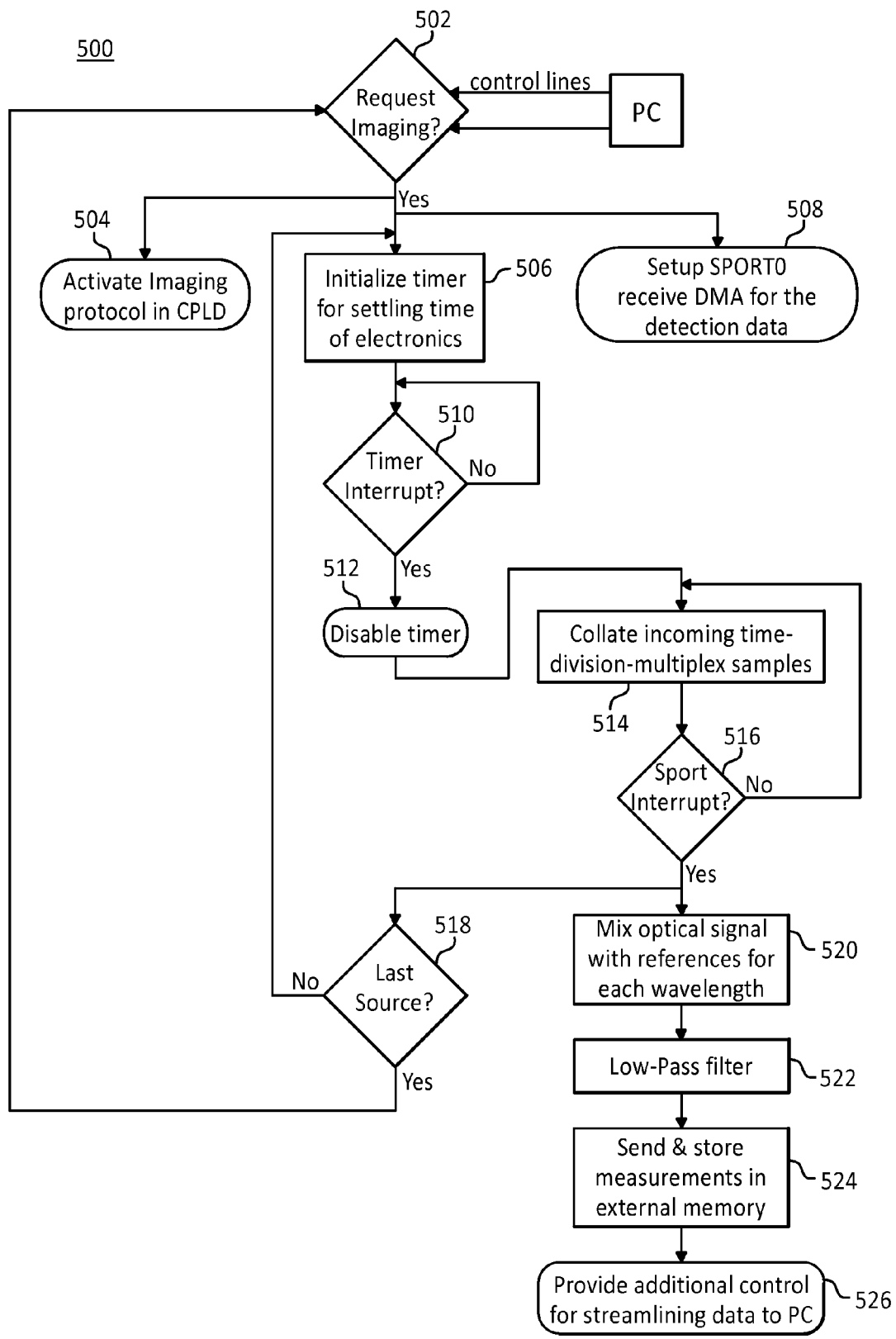
Fig. 5 — DSP-Imaging Routine

700

702 — Use a Digital Lock-In Filter with the following constraints that is ideal for discrimination of frequency encoded sources (different wavelength λ)

$$f_{\lambda i} = m_i \frac{f_s}{K}$$

$f_{\lambda i}$ = Modulation frequency
$f_s$ = ADC sampling frequency
K = Number of samples per source
$m_i$ = integer      $1 < m_i < K/2$
Filter Settling time $T_F = K/f_s$
    use $f_s$ = 75 KHz, K = 150 samples
$f_{\lambda i} = m_i$ * .5 KHz, $T_F$ = 2 ms

704 — The algorithm extracts from the measured signal M[k], the amplitude $A_{\lambda i}$ of the component due to wavelength λi.

706 — Store K values for cosine and sine wave at frequencies $f_{\lambda i}$.

708 — Modulate M[k] by the stored signals and then pass through an averaging filter.

710 — Use quadrature rule to produce phase shift independent amplitude.

$$I_{\lambda i} = \frac{1}{K} \sum_{k=1}^{K} \left( M[k] \cos\left[2\pi \frac{f_{\lambda i}}{f_s} k \right] \right),$$

$$Q_{\lambda i} = \frac{1}{K} \sum_{k=1}^{K} \left( M[k] \sin\left[2\pi \frac{f_{\lambda i}}{f_s} k \right] \right),$$

$$A_{\lambda i} = 2\sqrt{I_{\lambda i}^2 + Q_{\lambda i}^2}.$$

Lock-In Algorithm

Fig. 7

Averaging Filter Frequency Response

DIGITAL SIGNAL PROCESSOR-BASED DETECTION SYSTEM, METHOD, AND APPARATUS FOR OPTICAL TOMOGRAPHY

PRIORITY APPLICATION

This application claims priority to U.S. Provisional Patent Application No. 60/561,989, filed on Apr. 13, 2004, which is hereby incorporated herein by reference in its entirety.

FEDERALLY SPONSORED RESEARCH OR DEVELOPMENT

The invention disclosed herein was made with U.S. Government support under NIH Grant No. ROI-AR46255. Accordingly, the U.S. Government may have certain rights in this invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

This invention relates in general to optical tomography, and in particular to systems, methods and apparatuses that perform digital detection for use in optical tomography.

Optical tomography, or optical tomographic imaging, is often performed by measuring the amplitude attenuation of light that has been passed through tissue. Propagation of injected photons is determined by the spatially-varying absorption and scattering characteristics of the tissue being probed. In biological tissues, scattering interactions are often the principal mechanisms affecting the light trajectory. As a result of this highly scattering nature, these photons do not navigate in a straight procession but rather diffuse throughout the medium. The photon flux exiting the tissue at any single point is the net effect of the incident light source, and discrete absorption and scattering interactions throughout their pathlength. By illuminating several locations around the tissue of interest, and detecting transmitted and back-reflected intensities at multiple positions along the surface, one can generate tomographic images, similar to X-ray computed tomography. The transmitted intensity measured along the target surface maintains the same frequency with respect to the source, however, it will exhibit an amplitude attenuation and an induced phase shift. This amplitude attenuation and phase shift provide spatial information regarding the absorption and scattering distribution inside the tissue. In continuous wave imaging, the light is either illuminated at a constant amplitude or modulated by a low frequency sine wave (up to a few kHz), and the decay in amplitude relative to the incident source is measured. If the illuminated source is modulated, then a synchronous or homodyne detection technique is often employed to extract the zero-frequency amplitude information. This method requires generating a reference signal whose frequency is equal to and phase locked with the input waveform. Multiplying the input waveform by its reference signal produces an output waveform that is a composite of two independent contributions; one component located at zero-frequency and the other component straddling twice the modulation frequency. This resulting mixed signal is then sent through a low-pass filter to eliminate the higher frequency component, leaving only the remaining DC constituent whose amplitude is directly proportional to the amplitude of the detected optical signal. By imaging with multiple wavelengths, the spectral information is increased allowing investigators to formulate qualitative assessments of hemoglobin parameters such as oxyhemoglobin and deoxyhemoglobin, or quantitative valuations of additional physiologic chromophores. Each wavelength must be modulated at distinct frequencies and/or phase in order to isolate the individual signals and their respective amplitudes.

Almost all continuous wave optical tomography systems currently cited in literature perform any relevant signal conditioning and data processing through analog techniques. Analog systems are used to collect, condition, and possibly filter the incident signal. For those instruments that modulate the intensity of their light source, analog phase-sensitive lock-in methods are usually employed to extricate the optical signal obscured by noise of potentially greater magnitude.

Such analog detection systems, however, suffer from a number of deficiencies and limitations. More specifically, for example, analog phase sensitive detection has many problems associated with it that adversely affect their performance and restrict subsequent applications. Some primary deficiencies include, for example, signal drift, output offsets, gain error, limited dynamic reserve, and harmonic rejection. Additionally, external parameters such as temperature or age contribute to analog noise and, consequently, measurement uncertainty. Furthermore, analog processing is notably sensitive to component tolerances thereby limiting functional utility. Finally, when the digital timing signals share a backplane with analog data signals, coupling can occur causing fluctuations along the analog lines. A direct consequence of these undesirable attributes is that the instrument noise floor is elevated, causing a reduction in the detection sensitivity, diminished dynamic range for the overall system, and a slowing of the data acquisition. Analog detection systems suffer from other deficiencies and limitations, as well.

There is a need for detection systems for optical tomography that are better than existing detection systems.

SUMMARY OF THE INVENTION

In some embodiments, the invention provides systems, methods and apparatuses that perform digital detection for use in optical tomography. Methods and systems are provided in which digital lock-in detection is performed using an algorithm that employs a phase-independent quadrature technique; however, the invention also contemplates other phase-sensitive detection or lock-in techniques. In some embodiments, a unique manipulation of an ordinary averaging filter optimized for sources discrimination and the consequent sampling constraints is presented as a novel filtering scheme for the lock-in detection; however, the invention also contemplates other filtering schemes. Systems and apparatuses are provided which include a digital signal processor which performs digital lock-in detection, data handling, and system management, and an integrated complex programmable logic device for timing control. Apparatuses are provided which include an instrument having an integrated digital signal processor for performing digital processing and detection for use in optical tomography.

In one embodiment, the invention provides a digital detection method for use in optical tomography, including obtaining an analog signal to contain information. The method further includes performing digital processing and detection on the digital signal to facilitate obtaining information from the digital signal.

In another embodiment, the invention provides a digital detection method for use in optical tomography that employs embedded signal processing by means of an integrated digital signal processor.

In another embodiment, the invention provides a digital data-acquisition method for use in optical tomography.

In another embodiment, the invention provides a lock-in detection method for use in optical tomography, including obtaining an analog signal modulated to contain information. The method further includes performing digital lock-in detection on the digital signal to facilitate obtaining the information from the digital signal.

In another embodiment, the invention provides a lock-in detection method for use in optical tomography, including obtaining an analog signal modulated to contain optical tomographic information. The method further includes performing digital lock-in detection on the digital signal to facilitate obtaining the optical tomographic information from the digital signal.

In another embodiment, the invention provides a lock-in detection method for use in optical tomography, including obtaining an analog signal modulated to contain optical tomographic information. The method further includes amplifying the analog signal. The method further includes filtering the amplified analog signal using a low-pass filter. The method further includes converting the filtered analog signal into a digital signal. The method further includes performing digital lock-in detection on the digital signal to facilitate obtaining the optical tomographic information from the digital signal.

In another embodiment, the invention provides a lock-in detection method for use in optical tomography, including obtaining an analog signal modulated to contain optical tomographic information. The method further includes amplifying the analog signal. The method further includes filtering the amplified analog signal using a low-pass filter. The method further includes converting the filtered analog signal into a digital signal. The method further includes performing digital lock-in detection on the digital signal to facilitate obtaining the optical tomographic information from the digital signal. Performing digital lock-in detection includes using a lock-in algorithm employing a phase-independent quadrature technique and sampling constraints that optimize an averaging filter for source discrimination.

In another embodiment, the invention provides a lock-in detection system for use in optical tomography, including a low-pass anti-aliasing filter, an analog to digital converter, and a digital signal processor. An analog signal modulated to contain optical tomographic information is input to the low pass filter to obtain a filtered output analog signal. The filtered output analog signal is input to the analog to digital converter to be converted into an output digital signal. The output digital signal is input to the digital signal processor to perform digital lock-in detection on the digital signal to facilitate obtaining the optical tomographic information from the digital signal.

In another embodiment, the invention provides a lock-in detection system for use in optical tomography, including a trans-impedance amplifier, a programmable gain amplifier, a low-pass anti-aliasing filter, an analog to digital converter, and a digital signal processor. An analog signal modulated to contain optical tomographic information is input to the trans-impedance amplifier for amplification to obtain a first output amplified analog signal. The first output amplified analog signal is input to the programmable gain amplifier for amplification to obtain a second output amplified analog signal. The second output amplified analog signal is input to the low pass filter to obtain a filtered output analog signal. The filtered output analog signal is input to the analog to digital converter to be converted into an output digital signal. The output digital signal is input to the digital signal processor to perform digital lock-in detection on the digital signal to facilitate obtaining the optical tomographic information from the digital signal.

In another embodiment, the invention provides an apparatus for use in optical tomography, including a low-pass anti-aliasing filter, an analog to digital converter; and a digital signal processor. An analog signal modulated to contain optical tomographic information is input to the low pass anti-aliasing filter to obtain a filtered output analog signal. The filtered output analog signal is input to the analog to digital converter to be converted into an output digital signal. The output digital signal is input to the digital signal processor to perform digital lock-in detection on the digital signal to facilitate obtaining the optical tomographic information from the digital signal.

In another embodiment, the invention provides an apparatus for use in optical tomography, including a trans-impedance amplifier, a programmable gain amplifier, a low-pass anti-aliasing filter, an analog to digital converter; and a digital signal processor. An analog signal modulated to contain optical tomographic information is input to the trans-impedance amplifier for amplification to obtain a first output amplified analog signal. The first output amplified analog signal is input to the programmable gain amplifier for amplification to obtain an second output amplified analog signal. The second output amplified analog signal is input to the low pass filter to obtain a filtered output analog signal. The filtered output analog signal is input to the analog to digital converter to be converted into an output digital signal. The output digital signal is input to the digital signal processor to perform digital lock-in detection on the digital signal to facilitate obtaining the optical tomographic information from the digital signal.

In another embodiment, the invention provides an apparatus for use in optical tomography, including a low-pass anti-aliasing filter for receiving an analog signal modulated to contain optical tomographic information, and for filtering the analog signal to generate a filtered analog signal. The apparatus further includes an analog to digital converter, communicatively connected to the low-pass anti-aliasing filter, for receiving the filtered analog signal, and for converting the filtered analog signal into a digital signal. The apparatus further includes a digital signal processor, communicatively connected to the analog to digital converter, for receiving the digital signal, and for performing digital lock-in detection on the digital signal to facilitate obtaining the optical tomographic information from the digital signal.

In another embodiment, the invention provides an apparatus for use in optical tomography, including a trans-impedance amplifier for receiving an analog signal modulated to contain optical tomographic information, and for amplifying the analog signal to generate a first amplified analog signal. The apparatus further includes a programmable gain amplifier, communicatively connected to the trans-impedance amplifier, for receiving the first amplified analog signal, and for amplifying the first amplified analog signal to generate a second amplified analog signal. The apparatus further includes a low-pass anti-aliasing filter, communicatively connected to the programmable gain amplifier, for receiving the second amplified analog signal, and for filtering the second amplified analog signal to generate a filtered analog signal.

The apparatus further includes an analog to digital converter, communicatively connected to the low-pass anti-aliasing filter, for receiving the filtered analog signal, and for converting the filtered analog signal into a digital signal. The apparatus further includes a digital signal processor, communicatively connected to the analog to digital converter, for receiving the digital signal, and for performing digital lock-in detection on the digital signal to facilitate obtaining the optical tomographic information from the digital signal.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 5 is a flow diagram depicting a digital signal processor-based Imaging routine, according to one embodiment of the invention;

FIG. 7 is a flow diagram depicting a lock in algorithm, according to one embodiment of the invention;

DETAILED DESCRIPTION OF THE PREFERRED EMBODIMENTS

In the following description of the preferred embodiments, reference is made to the accompanying drawings that form a part hereof, and in which is shown by way of illustration a specific embodiment in which the invention may be practiced. It is to be understood that other embodiments may be utilized and structural changes may be made without departing from the scope of the present invention.

Herein, some embodiments of the invention, or aspects thereof, are described, or described in part, with the aid of reference to the prior art publication, C. H. Schmitz, M. Löcker, J. M. Lasker, A. H. Hielscher, R. L. Barbour, "Instrumentation for fast functional optical tomography," Review of Scientific Instruments, Vol. 73, pp. 429-439 (2002), which is hereby incorporated herein by reference in its entirety (which publication is hereinafter referred to as "Schmitz 2002"). Some embodiments of the invention, for example, are described as additions to, or modifications of, the system described therein, or aspects thereof.

It has been recently recognized that there is a need for detection systems for optical tomography that are better than existing analog detection systems. Some embodiments of the invention provide, for example, digital processing and acquisition methods which are better than existing analog detection systems.

Figure 1:
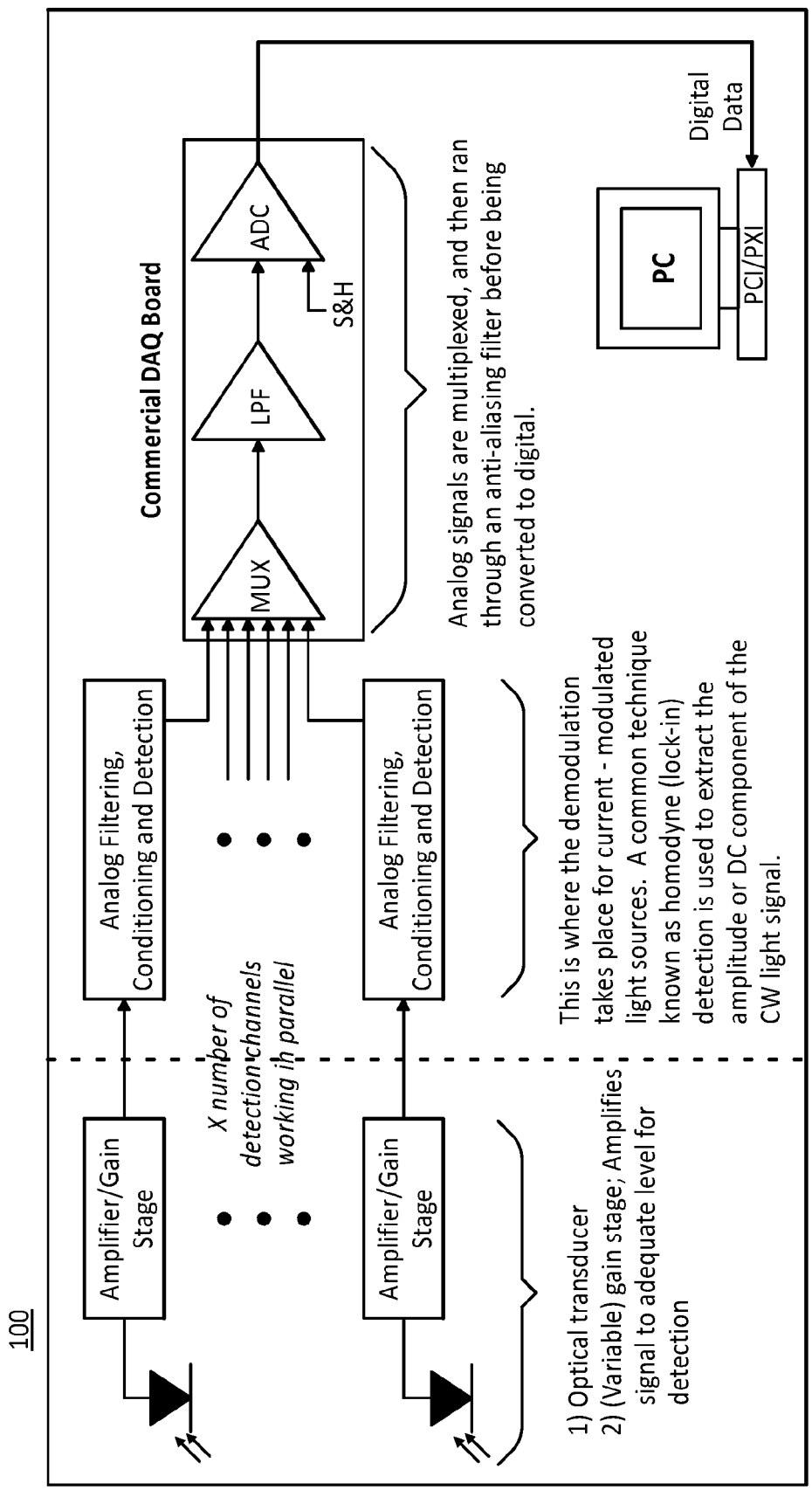
FIG. 1 is a block diagram depicting a prior art analog detection system used in optical tomography.
Figure 2:
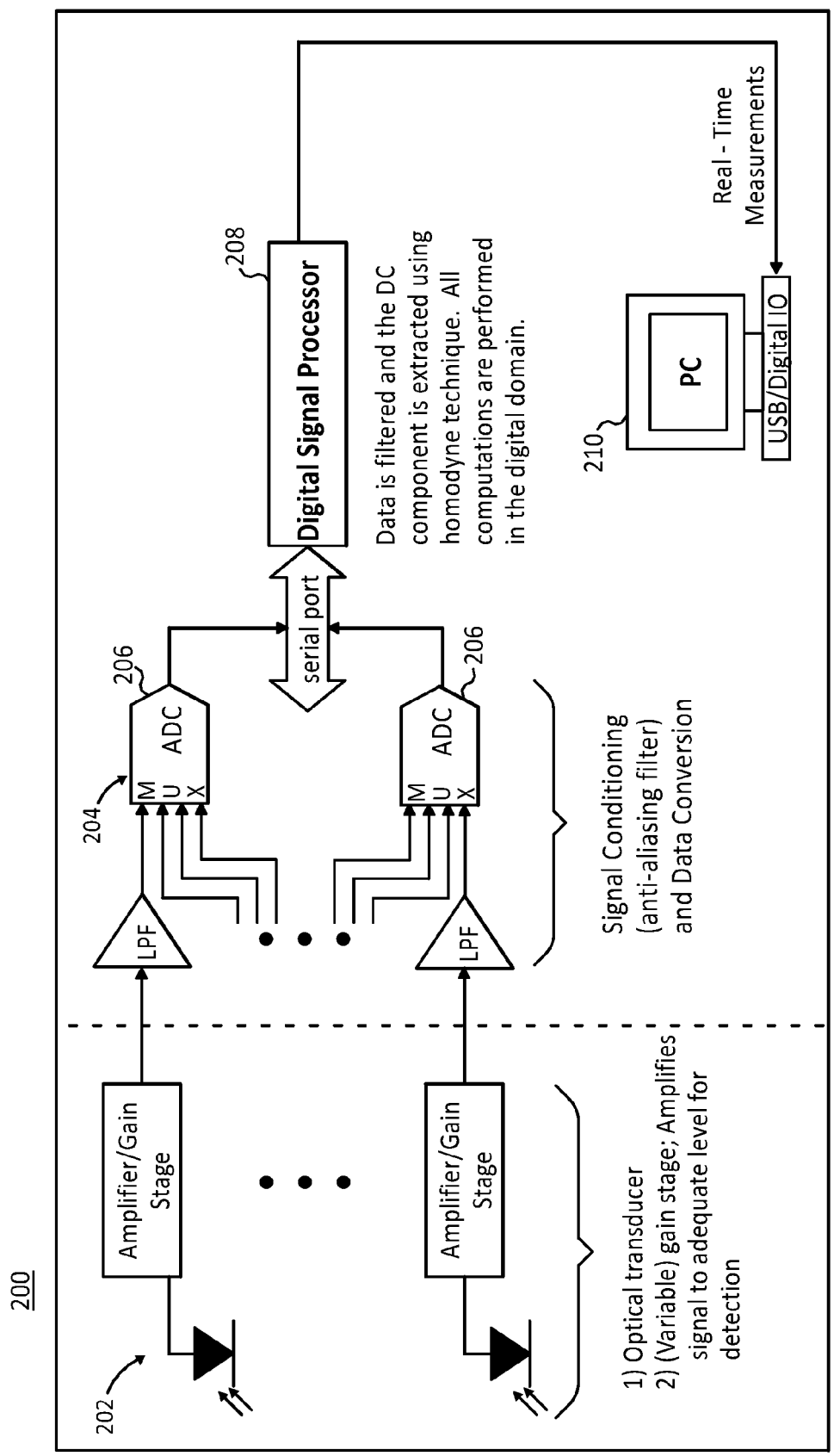
FIG. 2 is a block diagram of an optical tomography system that uses digital detection, according to one embodiment of the invention.

FIG. 1 (prior art) and FIG. 2 are referenced in comparing the conventional analog detection scheme with a digital detection scheme according to embodiments of the invention. FIG. 1 (prior art) is a block diagram depicting a prior art analog detection system 100 used in optical tomography. Even though the analog layout shown in FIG. 1 is typical for many measurement devices, a focus will be on a direct comparison between systems according to embodiments of the invention and instrument described in Schmitz 2002. The instrument described in Schmitz 2002 is essentially a first generation optical tomographic imager, and reference to it will aid in understanding some embodiments of the present invention, or aspects thereof.

To make quantifications of biological or physiological processes, a transducer is generally required to convert modified parameters into a detectable measurement. In some cases, the modified parameter is photon flux. For example, a light source may be directed at a specific tissue or limb of interest and the attenuated light exiting the tissue is detected at multiple positions along the surface. These measurements are then fed through an image reconstruction algorithm whose results impart insight into anatomic structure or physiologic conditions. Imaging with multiple wavelengths allows one to perform spectral analysis and quantify changes in hemoglobin parameters such as oxy and deoxy-hemoglobin, or other biological chromophores.

The light sources utilized with the instrument described in Schmitz 2002 can be, for example, laser diodes emitting light at wavelengths in the 700 nm-850 nm range. The laser diodes are amplitude-modulated at specific frequencies. Modulating the light source permits the use of lock-in (homodyne) detection which is a technique used to extricate signals of specific frequencies buried in noise of potentially greater magnitude.

On the detection end, multiple detector channels operating in parallel can be employed. The system described in Schmitz 2002 offers 32 channels; however, such a system can be easily extended to a larger number of channels. A photodiode is used to convert the light energy into a current that can be measured. A gain stage is required to bring the incoming signal to a detectable level, i.e. above system noise floor. Additionally, the amplification serves to increase the dynamic range of the instrument and maximize the sensitivity. The appropriate gain for a given channel is dependent on the target geometry, tissue density, and the detector's proximity to the light source and must be updated as the source position changes. A variable trans-impedance stage followed by a programmable amplifier offer a multitude of possible signal gains. Once the signal is adequately amplified, the DC value or amplitude can be extracted from it.

With respect to the instrument described in Schmitz 2002, after the incoming signal has been amplified appropriately, it goes through an analog lock-in filter which consists of several stages. Initially, the signal is mixed with a 'reference' signal of identical frequency to the one being extracted (one reference for each wavelength). The affect of this mixing procedure is that the resulting signal now has two components. The first component is sitting at DC. The second component is a sinusoid at twice the modulation/reference frequency. In the second stage, the mixed signal goes through a low-pass filter to remove the higher frequency component. All that remains is the DC component whose magnitude is directly proportional to the magnitude of the input signal and the phase difference between the input signal and reference.

The Instrument described in Schmitz 2002 employs a phase-shifter to minimize this phase difference and maximize the output. This procedure is executed for each wavelength. In embodiments of the present invention, as described below, however, another lock-in method which includes a quadrature-based detection technique can be used that would eliminate the need for this phase-shifter. To fully appreciate these techniques, a mathematical synopsis is provided herein.

Now that the magnitude information has been obtained, in some embodiments, it must be read into a computer and stored in a file. This is accomplished via a commercially available data-acquisition board. These boards have numerous analog input channels. For example, the instrument described in Schmitz 2002 uses one with 64, (32 channels×2 wavelengths). The DAQ board utilizes on-board multiplexers to sequence the sampling events for all inputs. Before it is digitized by an analog-to-digital converter (ADC), it must pass through an anti-aliasing filter to ensure that the signal conforms to the Nyquist constraints. The digitized samples are temporarily stored in a buffer and streamlined into the memory space of the host computer. This process is controlled by the DAQ software, LabVIEW, available from National Instruments Corp.

FIG. 2 is a block diagram of an optical tomography system 200 (a system used in or for optical tomography, or aspects thereof) that uses digital detection, according to one embodiment of the invention. As depicted in FIG. 2, instead of performing further analog conditioning, the modulated signal is to be digitized immediately following programmable gain segment 202. As generally required for any properly constructed digital conversion process, an anti-aliasing filter must be included, and is depicted as included in segment 204. ADC 204 samples the analog channels two at a time. Data samples get clocked out of the ADC and into the DSP 208 via a serial port connection. Once in the DSP 208, it goes through a digital lock-in filter which also consists of a mixing process and low-pass filter. Upon completion of all computations, the DSP 208 sends out the data to the host PC 210 for storage, display, and image reconstruction.

A comprehensive description of the instrument design and engineering, according to some embodiments of the invention, follows. System specifications are presented initially, to demonstrate rationale behind the development of the new imager. Included are detailed sections explaining design, as well as component selection for a trans-impedance amplifier, programmable-gain amplifier, anti-aliasing low-pass filter, and analog-to-digital converter, according to embodiments of the invention.

Some embodiments of systems according to the invention include components or design features that are replaced or re-designed with different components, relative to components or design features of the instrument and system described in Schmitz 2002, or relative to components or features which may be used in a typical analog system 100 as depicted in FIG. 1 (Prior Art).

Generally, in redesigning the analog detector boards relative to analog detector boards such as those used in the instrument described in Schmitz 2002, the following improvements, modifications, or changes are made. It is to be noted, however, that these improvements, modifications, or changes are not intended to be a comprehensive or complete listing.

One change is that the electrical noise on each channel is decreased. This noise consists of two components: one is the intrinsic noise generated by the electronics themselves and the other is extrinsic noise, radiated from some outside source.

Another change is that the settling time of each channel after a change in source positions is decreased thereby increasing the temporal resolution. This settling time is the limiting factor determining overall image frame rate. The input channels of the instrument described in Schmitz 2002 settle in about 10 ms due to the source switch and the hardware lock-in amplifier.

Another change is that the size of the system is decreased. An instrument according to some embodiments of the invention has one analog detection channel per circuit board using through-hole components. By using surface-mount components, four analog channels per board are to be used, decreasing the number of total boards.

Another change is that the input dynamic range of the system is increased. It can be difficult to saturate the detector channels when the optical signal is large.

Another change is that the overall power consumption of the analog detector boards is decreased by reducing the power supplies from +/−18V to +−5V. This may help prevent board heating and reduce drift due to temperature changes.

Another change is that the superior performance of digital filtering is utilized to process incoming data and to perform the homodyne detection. Keeping the wavelength capacity of the instrument described in Schmitz 2002, the instrument was designed to accommodate up to four modulation frequencies. Adding more wavelengths would be straightforward, and some embodiments of the invention use additional frequencies. The software lock-in amplifier to be used dictates various constraints on the modulation frequencies and the number of samples to be acquired. Therefore, defining a modulation bandwidth in the range from 3 kHz to 9 kHz allows some flexibility in choosing modulation frequencies and the number of samples.

It is to be understood that the improvements, modifications, or changes described above are not intended to be a comprehensive or complete list.

Figure 3:
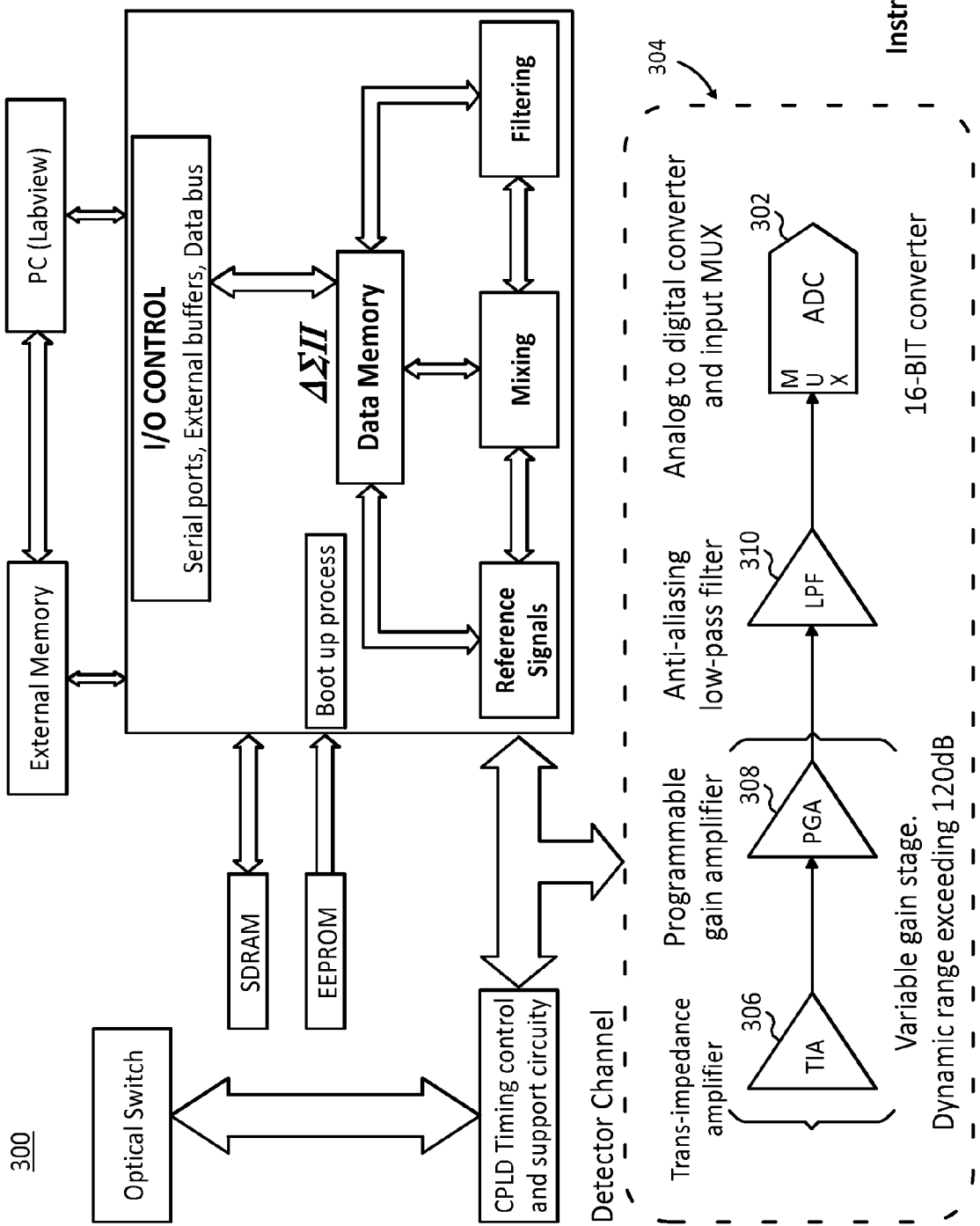
FIG. 3 is a block diagram of an instrument layout for an optical tomography system that uses digital detection, according to one embodiment of the invention.

FIG. 3 is a block diagram of an instrument layout for an optical tomography system 300 that uses digital detection, according to one embodiment of the invention. One systemic change, relative to the instrument described in Schmitz 2002, for example, is that the analog-to-digital converter (ADC) function is moved to the analog detector boards, such as ADC 302 of detector channel 304, as depicted in FIG. 3. Each ADC has an internal 4-channel MUX, so that four detector channels can be included on each detector board. Each detector channel will consist of a trans-impedance amplifier (TIA), a programmable-gain amplifier (PGA), a low-pass filter (LPF), and the ADC 302. For example, as depicted in FIG. 3, the detector channel 304 includes TIA 306, PGA 308, LPF 310, and the ADC 302.

Figure 4:
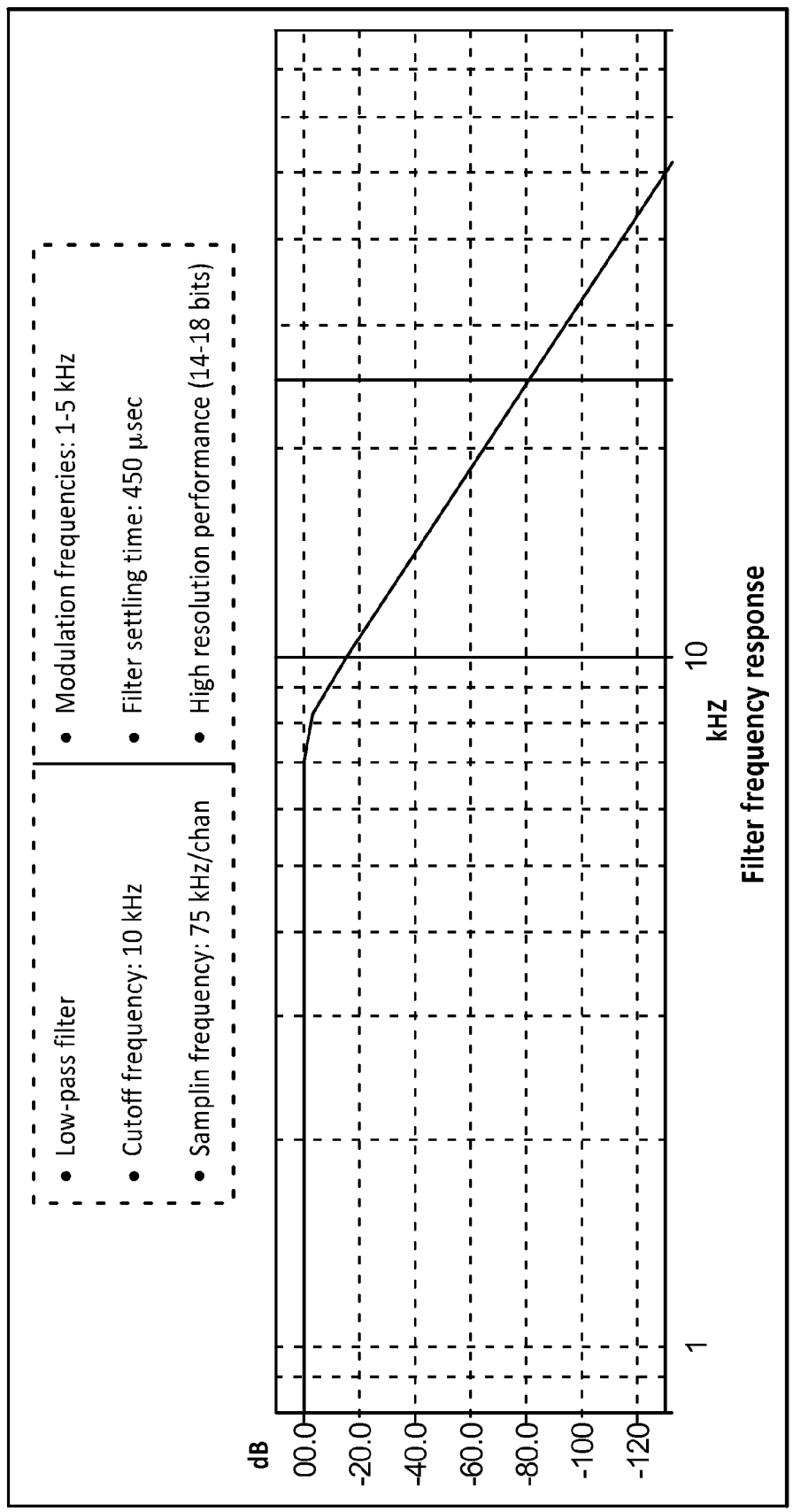
FIG. 4 is a graph depicting filter frequency response of an anti-aliasing filter, according to one embodiment of the invention.

FIG. 4 is a graph 400 depicting filter frequency response of a low pass anti-aliasing filter according to one embodiment of the invention.

In previous systems, such as the system 100 depicted in FIG. 1, analog signals were passed through a backplane and eventually to an ADC card on a host PC. By putting an ADC on each analog detector board, as is done according to some embodiments of the invention, the amount of noise picked up between the Analog Detection Boards (ADB) and the host PC is reduced (digital data transmission has much better noise immunity). This helps to decrease the extrinsic noise on each channel.

Another system change, according to some embodiments of the invention, is to move the lock-in amplification (LIA) function from hardware to software. By performing it in software, numerous benefits are achieved. One benefit is a decrease in the settling time of the detector electronics. Preliminary LIA code shows settling times in the 1-2 ms range as opposed to 7 ms in the hardware LIA of the instrument described in Schmitz 2002. In some embodiments, the rest of the electronics in a digital detector board, according to some embodiments of the invention, take from 2-4 ms to settle (determined by the high-pass filter at the TIA output—this can probably settle simultaneously with the source switch). The overall settling time of the system's detector electronics according to some embodiments of the invention (not including the source switch) is between 3 ms and 6 ms (easily adjustable within this range by minor differences in the design). Another benefit to moving the LIA to software, as is done in some embodiments, is a decrease in the complexity of the ADB. Furthermore, significant performance benefits can be realized by implementing the LIA in the digital domain. This is a result of eliminating the adverse analog effects of the analog electronics, analog signal processing, and filter chips—and being able to customize the filter for user-specific applications. To increase the system's input dynamic range, according to some embodiments of the invention, a third gain setting for the TIA is included. This 1-kΩ gain setting will be included with the previous 10-kΩ and 10-MΩ gain settings.

The following is a description of aspects of a TIA according to some embodiments of the invention, such as the TIA 306 depicted in FIG. 3, as referenced above.

In the system described in Schmitz 2002, there are two values of Rf (trans-impedance feedback resistor) to choose from, spaced by a factor of 1000 (10 kΩ and 10 MΩ). The TIA gain is multiplied by the gain of the PGA, which can be 1, 10, 100 or 1000. This allows overall gains from 10 kV/A to 10 GV/A spaced by a factor of ten.

In systems according embodiments of the invention, such as the system 300 depicted in FIG. 3, as referenced above, there are three values of TIA Rf to choose from (1 kΩ, 10 kΩ and 10 MΩ). The PGA 308 of system 300 only has three gain settings (1, 10 and 100). This allows for overall gains ranging from 1 kA/V to 1 G\A/V spaced by a factor of 10. Using the 1 kΩ resistor results in a 10 times larger input dynamic range at the lowest gain setting. One motivation for this additional gain flexibility is the realization that when performing measurements on small geometries (1 cm-3 cm) as is common with small animal imaging, the TIA stage will readily saturate for small optode separations and intensity filters must be introduced. By increasing the dynamic range of the TIA 306 through this 1 kΩ resistor, a reason is to eliminate the need for any optical filters thereby making the instrument suitable for imaging small animals as well as large tissue structure. The PGA gain setting of 1000 has been omitted in the new system because the noise levels at this gain setting become too high to achieve 1% linearity in many cases.

Another change or improvement, in systems according to embodiments of the invention, is to extend the bandwidth of the TIA 306 at its highest gain setting (10 MΩ). In the instrument described in Schmitz 2002, the BW was limited to 16-kHz by a 1-pF feedback capacitor in parallel with the 10 MΩ resistor. This capacitance cannot be reduced much because parasitic board capacitances can be between 0.5 pF and 3 pF anyways.

For the TIA 306 depicted in FIG. 3, in order to achieve three TIA gain settings, two reed relays ($K_1$ and $K_2$) are used to switch the three feedback resistors ($R_1$, $R_2$ and $R_3$). These reed relays are controlled by an 8-1 analog MUX and three gain bits. When one of the MUX's analog inputs is selected, the corresponding reed relay coil is grounded through the MUX. This allows the relay coil to conduct, closing the switch. When $K_1$ or $K_2$ is activated, $R_1$ or $R_2$ is placed in parallel with $R_3$. Since $R_1$ and $R_2$ are both at least 1000 times lower than $R_3$, it follows that $R_1$ or $R_2$ sets the gain of the TIA when $K_1$ or $K_2$ is activated. In some embodiments, only one reed relay switch can be closed at a time (because only one channel of the 8-1 MUX can be selected at a time). In some embodiments, since the reed relays consume more current than any other circuit element, it is significant that only one can be activated at a given time. When neither of the relays is closed, $R_3$ sets the TIA gain.

For the TIA 306 depicted in FIG. 3, the TIA circuit consists of an op-amp, two reed relays, a MUX, and various passive components. The following includes an explanation of component selections. In some embodiments of the invention, a photodiode such as that used and described in Schmitz 2002 is utilized.

For the TIA 306 as depicted in FIG. 3, the op-amp ($IC_1$) utilized has a very low input bias current. This is important when trying to accurately measure photodiode currents in the tens of picoamps range. The op-amp also has low voltage noise and low current noise. With a 10 MΩ feedback resistor, this current noise generates a voltage noise of 7 uV. This is less than the resistive thermal noise of the 10 MΩ resistor. It is believed that the current noise increases with temperature so it is important to keep the temperature not much higher than 25° C.

The following is a description of a PGA that can be utilized in embodiments of the invention, such as the PGA 308 as depicted in FIG. 3.

As mentioned in the TIA discussion, PGA gains are to be had of 1, 10 and 100, instead of the PGA gains of the instrument described in Schmitz 2002 of 1, 10, 100 and 1000. To implement the PGA 308, an instrumentation amplifier (gain programmed by a resistor) is used; an 8-1 MUX; and various passive components. The integrated PGA as used in the instrument described in Schmitz 2002 is not used, in some embodiments of the invention, for at least a few reasons, as follows. First, the integrated PGAs tend to have fairly high supply currents. Second, many PGAs have relatively low input impedances. Low input impedance is not good for the design because the input to the PGA is a 4.7 kΩ resistor and voltage division would result. Also, the PGA as included in the system described in Schmitz 2002 is relatively non-linear (0.015%, while 16-bit accuracy is about 0.0015%).

For the PGA 308, to change the PGA gain, the 8-1 MUX connects a different resistor between pins 1 and 8 of the instrumentation amplifier based on two control bits. The particular in-amp used for the PGA 308 is available from Texas Instruments, Inc., although other in-amps may be utilized in other embodiments of the invention. This amplifier has low quiescent current, low input bias current, low input offset voltage, low non-linearity, dual supply operation and a high gain-bandwidth product. The maximum quiescent current of 0.75 mA is almost a tenfold decrease in current consumption compared to the PGA 308.

The Analog Devices Model ADG608B MUX, available from Analog Devices, Inc., can be used as the analog MUX because it operates on ±5-V supplies and has an acceptable on-resistance (measured to be about 16 Ω). Operating on ±5-V supplies is important because the input can be positive or negative.

Resistors, according to some embodiments of the invention, are chosen for PGA gains of 1, 10 and 100 according to Equation (1):

$$G = 1 + \frac{50 \text{ k}\Omega}{R + 16 \text{ }\Omega} \quad (1)$$

The addition of 16 Ω in the denominator of Equation (1) is due to the on resistance of the MUX.

To change the PGA gain, the 8-1 MUX—governed by two control bits—connects a different resistor $R_G$ across the appropriate pins of the instrumentation amplifier. The following chart (Table 1) tabulates the total effective signal gain based on the values of all three control bits.

TABLE 1

| G2 | G1 | G0 | TIA gain (Ω) | PGA gain (V/V) | Overall Gain (Ω) |
|----|----|----|--------------|----------------|------------------|
| 0 | 0 | 0 | 1 k | 1 | 1 k |
| 0 | 0 | 1 | 10 k | 1 | 10 k |
| 0 | 1 | 0 | 10 k | 10 | 100 k |
| 0 | 1 | 1 | 10 k | 100 | 1 M |
| 1 | 0 | 0 | 10 M | 1 | 10 M |
| 1 | 0 | 1 | 10 M | 1 | 10 M |
| 1 | 1 | 0 | 10 M | 10 | 100 M |
| 1 | 1 | 1 | 10 M | 100 | 1 G |

In some embodiments, the appropriate gain values are determined prior to making a measurement and depend on the target geometry, tissue density, and the detector's proximity to the light source. These values for all detector channels must be updated for each source position. The corresponding bits are stored in local memory banks located on each detector card and made available for immediate access. Including the on-board memory cache into the modular structure of the detector cards has numerous advantages. First, it eliminates the need for a designated gainbit-routing board. Because of the substantial fan-out generated by such a routing board, it necessitates a sizable allotment of space and produces many parallel lines running throughout the instrument. Secondly, this modular format makes it very simple to add additional detector channels without requiring a system restructure. Furthermore, it is the most compact and efficient way of distributing the gainbit values.

The following description relates to aspects and specifications of an anti-aliasing LPF according to embodiments of the invention, such as the LPF 310 depicted in FIG. 3.

In some embodiments, the system 300 is designed to provide a signal passband from 3 kHz to 9 kHz (with 1% flatness). Since the TIA 306 sets the attenuation at 9 kHz to 1%, the attenuation at 9 kHz caused by the LPF stage is to be minimized. In some embodiments, the system 300 is designed to provide a 0.1% LPF attenuation at 9-kHz and as steep a roll-off as possible after 9 kHz while preserving flatness in the passband. This roll-off attenuates any noise above 9 kHz, aiding the LPF function implemented in the LIA. It also provides anti-aliasing before sampling of the signal with the ADC. Since the noise floor for an ideal 16-bit ADC is −96 dB, the system 300 is designed to provide at least this much attenuation at any frequencies that could alias to 9 kHz or below. The LPF 310 is designed to have a good time response to a step input (for when the source position and gain settings switch) and to settle to 16-bit accuracy in less than 1 ms with a full-scale step input. Also, the LPF 310 IC is designed to provide low-power and small size.

In some embodiments, The LPF 310 is implemented with an $8^{th}$ order Butterworth filter. The Butterworth filter topology tends to have the flattest passband and relatively steep roll-off. They also tend to have a fairly good time response to step inputs. An $8^{th}$ order filter is used because it is practical with the currently available filter ICs. Higher orders would require more filter ICs in series (increasing size and power consumption), while lower orders do not provide the necessary attenuation at frequencies just above 9 kHz. A cutoff frequency of 12.5 kHz is used to meet the specification of 0.1% LPF attenuation at 9 kHz. Assuming a sampling frequency of 75 ksps, noise appearing in the 67 kHz-72 kHz and could alias into the passband. However, this LPF more than adequately performs its antialiasing function (−117 dB attenuation at 67 kHz).

In some embodiments, the system 300 utilizes two 4th order filter ICs, cascaded to implement the $8^{th}$ order Butterworth LPF. These filter ICs have low noise and distortion (specified for 16-bit systems). They are continuous-time active filters so they do not suffer from clock noise as switched-capacitor filters do. In some embodiments, these $4^{th}$ order filter Ics are used instead of a single $8^{th}$ order IC because these have a low-power mode with a quiescent current of 2.2 mA each. This is considerably less current consumption than the lowest single-IC $8^{th}$ order continuous-time filters.

The following description relates to aspects and specifications of an ADC buffer according to embodiments of the invention.

In some embodiments, the system 300 incorporates a 2.5V offset into the input buffer of the ADC 302. Signals exiting the LPF 310 are centered about zero volts whose amplitude has an upper limit of $5V_{p-p}$. The ADC though, operates between 0V and +5V so we must add a 2.5V offset to form a pseudo-bipolar signal. This preserves the $5V_{p-p}$ now centered around 2.5 volts. The driver must be able to settle for a full-scale step of the capacitor array at a 16-bit level (0.0015%). Furthermore, the noise generated by the driver must be kept to a minimum in order to preserve the SNR performance of the ADC.

The following description relates to aspects and specifications of a DSP according to embodiments of the invention, such as the DSP 208 depicted in FIG. 2, as referenced above.

In some embodiments, the system 300 is designed to provide the highest possible resolution ADC while retaining the ability to sample at ≧50 ksps for each of four multiplexed channels. In some embodiments, the ADC 302 would preferably have at least a four-channel input multiplexer built-in. It should also have a serial output to the DSP 208. This will result in less digital data lines than a parallel data output. Low current consumption would also be helpful, but is not critical since there is only one ADC 302 per four detector channels.

In some embodiments, with respect to the ADC utilized, such as the ADC 302 depicted in FIG. 3, a 4-channel, 16-bit, 1 Msps ADC, is used. This is the fastest 4-channel, 16-bit ADC available at present. The effective number of bits of this ADC is about 14. This is sufficient because the noise floor of the analog electronics does not permit better than 14-bit resolution except for two gain settings (noise is dominated in most gain settings by the TIA feedback resistor). The 1 Msps sampling rate allows sampling of each channel at a sufficiently high rate (sampling is being done at ~75-80 ksps). It also has a relatively low current consumption.

The ADC's sample two channels simultaneously. Initially it samples the first two channels, whose samples are read into the DSP 208 over the serial port line. The mux is then switched and it samples and clocks out the remaining two channels.

The following includes a description of aspects and functions of a DSP and a complex programmable logic device (CPLD), according to some embodiments of the invention. It is through these devices where the multitude of tasks takes place for each source position and each imaging frame. These two devices require meticulously-orchestrated timed operations and must be in continuous communication with one another.

In some embodiments of the invention, the Digital Signal Processor (DSP) plays a substantial role in data acquisition timing and overall system control, providing or helping to provide a number of advantages to an instrument into which it is integrated, which can include computational power, flexibility, and speed.

In some embodiments, upon power up, the DSP goes through a boot-up sequence which loads the programming code into internal memory. This sequence is a set of instruction used to initialize and direct the loading of the DSP. This boot-sequence is stored in an on-board EEPROM and the DSP is programmed to download and read its contents when power is applied.

In some embodiments, the DSP goes through a series of system initialization processes so that registers are appropriately prepared for running experiments. These processes include:

1) Initialize CPLD;
2) Setup interrupt vector table;
3) Initialize programmable digital I/O lines;
4) Clear serial port registers;
5) Program serial port registers;
6) Program gain-bit DMA (Direct Memory Access);
7) Setup imaging DMA;
8) Setup timer;
9) Setup external port buffer;
10) Generate reference signals (for each wavelength); and
11) Go into standby.

In standby, the DSP is continuously polling the digital I/O fines connected to the PC waiting for an instruction. In some embodiments, there are three possible instructions.

A) Download Gain-bit values;
B) Start Imaging;
C) Stop Imaging;

In some embodiments, with respect to (A) Download Gain bit values, as mentioned above, the following operations are carried out for each request:

a. Gain-bit values are received from the PC, sent over the data bus through a relevant transfer protocol, and stored in DSP onboard memory.
b. DSP sends instruction word to CPLD and tells it to begin going through gain-upload sequence.
c. The gainbits for all channels are sent out from the DSP one source at a time and are routed to the detector boards by the CPLD. The DSP increments through the number of sources and then stops when all bits are uploaded. The gainbits are sent out over the serial port transmit line using a DMA protocol which has an independent processor so the DSP's core is not occupied with I/O responsibilities.

In some embodiments, with respect to (B) Start imaging, as mentioned above, the following operations are carried out for each request:

a. Send instruction word to CPLD over serial line and tell it to begin imaging process.
b. Initialize timer that counts 5 msec for the electronics and light source to settle.
c. Setup serial-port receive-DMA which is used to receive the digitized samples for all detector channels.
d. Wait for timer interrupt. Disable timer. CPLD controls sampling process and DSP waits for the data to come in over the serial port. Data coming into the DSP is time-division-multiplexed. The DMA channel is setup such that it collates the samples for each channel so that when sampling is complete, data is organized in the DSP's memory block.
e. When all data is received, another interrupt is generated that starts the lock-in algorithm. The DSP mixes the reference signals and the data samples. It filters the resulting signal with an averaging filter (more detail on that below) to discard the higher frequency components.
f. When processing is complete, data is sent to external memory via the data bus where it is streamlined into the host PC by either a USB controller or a digital I/O board. This too is sent out through means of a DMA procedure.
g. Steps b-f are repeated for all sources until the imaging frame is complete. After data from last source is received, the DSP check the digital I/O status line to see if it should image another frame.

In some embodiments, with respect to (C) Stop imaging, as mentioned above, the following operations are carried out for each request:

a. If control lines indicate termination of data acquisition, the DSP completes the frame it is processing and then stops. The CPLD does the same.
b. Return to standby.

In systems according to some embodiments of the invention, the CPLD acts as a multi-level state machine and can execute a variety of standard logic operations. Once enabled, the CPLD's main state machine enters standby mode. There it waits for an instruction from the DSP telling it to enter either the Gainbit or Imaging state-machines.

In some embodiments, after entering a Gainbit state machine, the CPLD performs the following:

a. Initialize FIFOs and shift registers.
b. Get number of sources for experiment from DSP.
c. Receive gainbit data from DSP and clocks them through the shift registers on the detection boards. When gain upload is complete, the CPLD writes them into their respective FIFOs where they are stored and used during the imaging routine. This procedure is executed successively, one source at a time for all activated sources positions.
d. Returns to standby in main state-machine.

In some embodiments, after entering a Gainbit state machine, the CPLD performs the following:

a. Move source switch into position.
b. Wait for settling time trigger from DSP.
c. Begin conversion/sampling sequence. Signals are sampled half the channels at a time being that each ADC sample two channels simultaneously. Digitized data is time-division multiplexed onto the DSP's serial port. As these samples are clocked into the DSP, the CPLD is updating the address of the ADC's mux. The next conversion signal read by the ADCs are used for the remaining channels. When all samples for all channels have been taken, the CPLD repeats steps a-c until imaging frame finishes in its entirety.

d. Goes into standby waits for another imaging instruction.

FIG. 5 is a flow diagram depicting a DSP-based Imaging routine 500, according to one embodiment of the invention. At step 502, it is inquired whether an imaging request has been issued.

If an imaging request has been made, the routine 500 proceeds to steps 504, 506, and 508. These steps include, respectively, activate imaging protocol in the CPLD, initialize timer for settling time of electronics, and setup SPORT (Serial Port) receive DMA for the detection data.

Following step 506, the routine 500 proceeds to step 510, at which it is queried whether a timer interrupt has been issued. If not, then the routine 500 remains in query step 510.

If a time interrupt has been issued, the routine 500 proceeds to steps 512 and 514, at which include, respectively, disable timer and collate incoming time-division multiplex samples.

Following step 514, the routine 500 proceeds to step 516, at which it is queried whether a SPORT interrupt has been issued. If not, then the routine remains at step 514.

If a SPORT interrupt has been issued, the routine 500 proceeds to step 520, which includes, mix optical signals with references for each wavelength.

Following step 520, the routine 500 proceeds to step 522, which includes utilization of the LPF, and also returns to step 518.

At step 518, it is inquired whether the source is the last source. If yes, then the routine 500 returns to step 502. If no, then the routine 500 returns to step 506.

At step 522, the low pass filter is utilized. Following step 522, the routine 500 proceeds to step 524, which includes sending & storing measurements in external memory.

Following step 524, the routine 500 proceeds to step 526, which includes providing additional control for streamlining data to a computer or computerized device, such as a personal computer (PC), or, in some embodiments, over one or more networks to one or more computing devices. Herein, wherever a PC is depicted or described, it is to be understood that the PC could be any computing device or devices, and could be reachable through or include one or more networks.

Figure 6A:
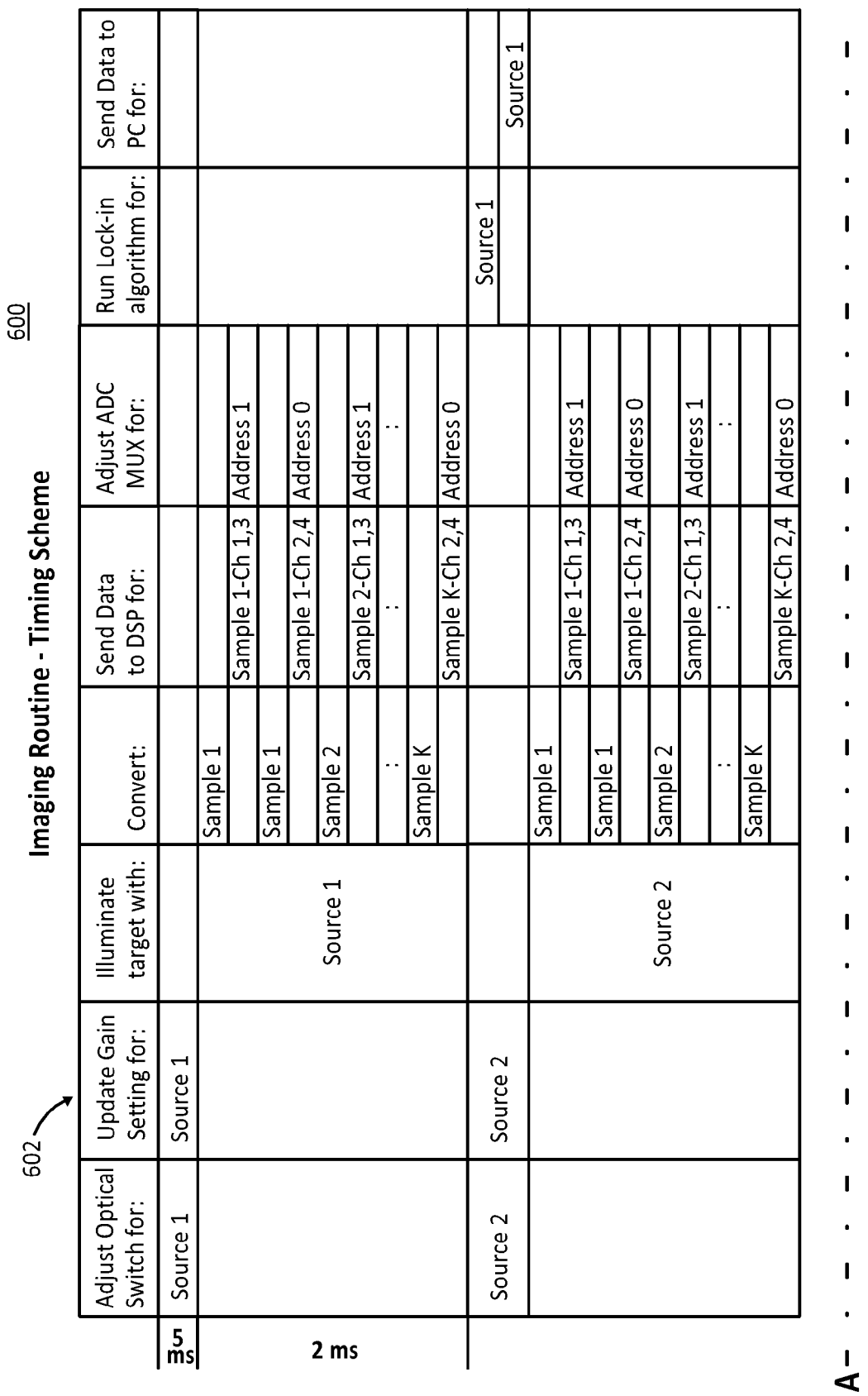
FIG. 6A and 6B is a table depicting a timing scheme for an imaging routine, according to one embodiment of the invention.
Figure 6B:
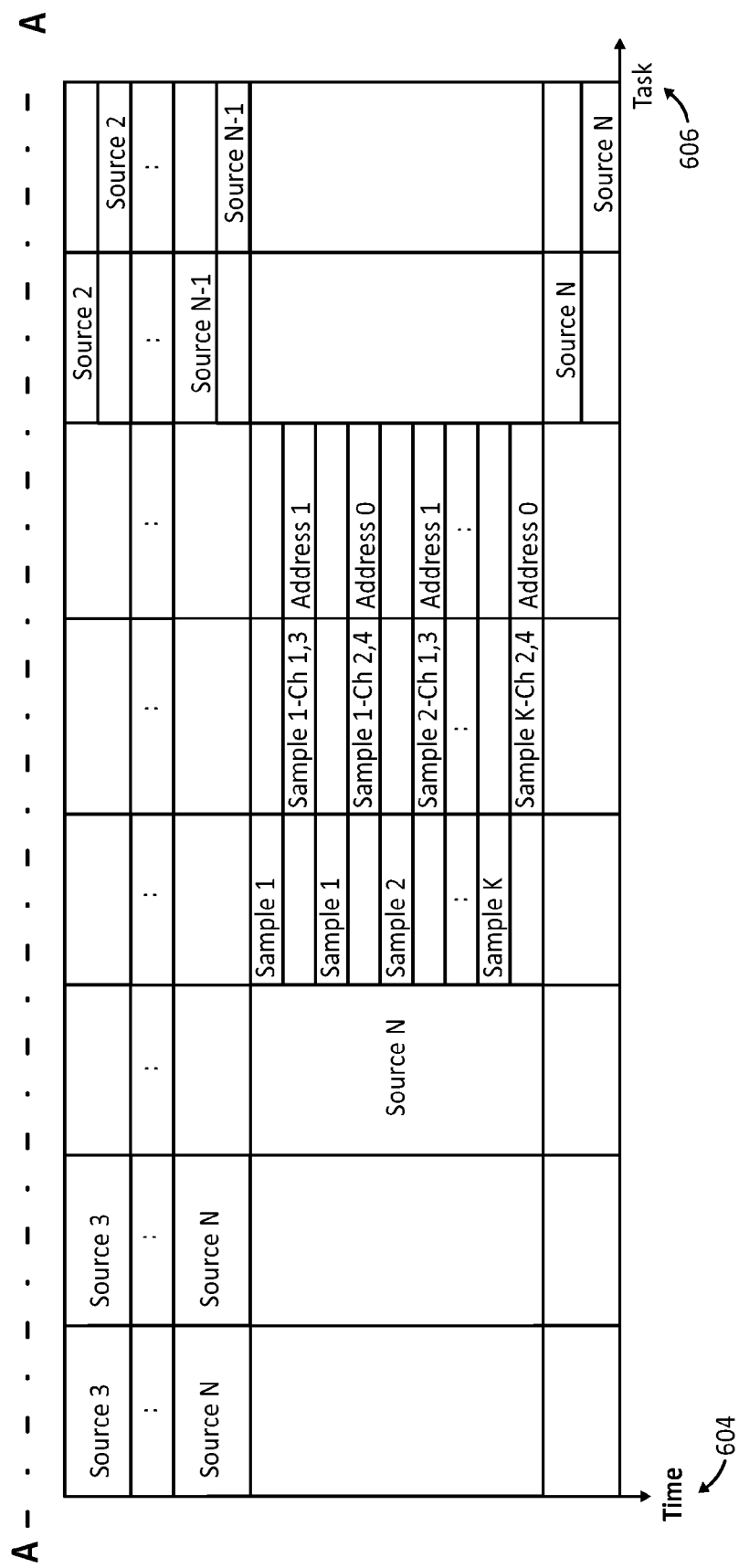

FIG. 6A and 6B is a table depicting a timing scheme 600 for an imaging routine, according to one embodiment of the invention. As depicted, the vertical axis 602 indicates time passing as the axis 602 proceeds downwardly, while each task 606 is indicated by an entry in the table 602 in a vertical position indicating the time or time period at which the task is performed or accomplished.

FIG. 7 is a flow diagram depicting one type of lock in algorithm 700, according to one embodiment of the invention.

At step 702, according to the algorithm 700, a digital lock-in filter is used with the following constraints, the filter being ideal for discrimination of frequency encoded sources (different wavelength λ):

$$f_{\lambda,i} = m_i(f_s/K), \text{ where:} \quad (2)$$

$f_{\lambda,i}$=Modulation frequency for source i;
$f_s$=ADC sampling frequency;
K=Number of samples per source;
$m_i$=positive integer for source i $1 < m_i < K/2$; and $$\text{Filter Settling time } T_F = K/f_s, \text{ where:} \quad (3)$$

use $f_s$=75 KHz, K=150 samples; and $f_{\lambda,i} = m_i * 0.5$ KHz, $T_F$=2 ms At step 704, the algorithm 700 extracts from the measured signal M[k] the amplitude $A_{\lambda,i}$ of the component due to wavelength λi.

At step 706, the algorithm stores K values for cosine (In-phase) and sine (Quadrature) wave at frequencies $f_{\lambda,i}$.

At step 708, M[k] is modulated by the stored signals forming quadrature components and then passed through an averaging filter in accordance with the following equations:

$$I_{\lambda i} = \frac{1}{K}\sum_{k=1}^{K}\left(M[k]\cos\left[2\pi\frac{f_{\lambda i}}{f_s}k\right]\right), \quad (4a)$$

$$Q_{\lambda i} = \frac{1}{K}\sum_{k=1}^{K}\left(M[k]\sin\left[2\pi\frac{f_{\lambda i}}{f_s}k\right]\right),$$

At step 710, the quadrature rule is finalized to produce phase-shift independent amplitude, in accordance with the following equation:

$$A_{\lambda i} = 2\sqrt{I_{\lambda i}^2 + Q_{\lambda i}^2}. \quad (4b)$$

Figure 8:
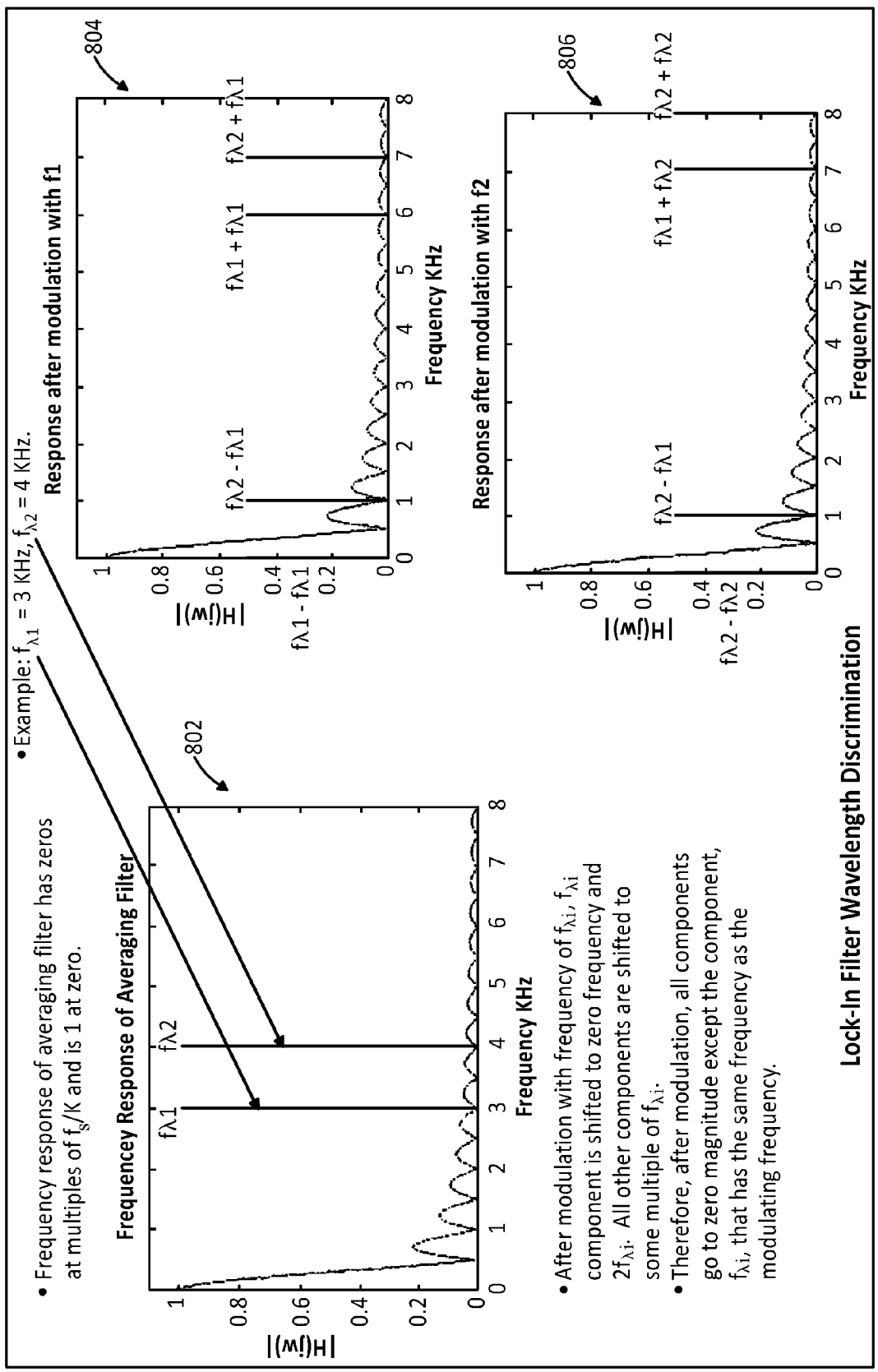
FIG. 8 is a set of graphs depicting lock-in filter wavelength discrimination, according to one embodiment of the invention.

FIG. 8 is a set of graphs 802, 804, 806 depicting lock-in filter wavelength discrimination, according to one embodiment of the invention.

It is to be noted that, in some embodiments, the lock in filter can be, but is not limited to, an ordinary averaging filter.

The averaging or mean filter is presented and described in detail such that its unique exploitation, according to some embodiments of the invention, is demonstrated. However, other digital filters, including but not limited to, cascaded RC filters, Bessel filters, critically damped filters etc., are utilized in some embodiments of the invention.

Other digital low-pass filter characteristics include, but are not limited to, Bessel and critically damped (CD) filters. Both are characterized by a good time-domain response, i.e. fast settling and little overshoot and ringing. A multi-order CD filter is used in some embodiments of the invention because it has superior step response characteristics (i.e. fast settling without overshoot) compared to other filter types. The CD filters' disadvantage of a slow roll off—a severe limitation of their use in analog implementations—is overcome, in some embodiments, by numerically cascading multiple filter stages. For example, a 20th-order CD filter has comparable roll-off characteristics to a 4th-order Butterworth at far superior settling characteristics (D G Robertson, J J Dowling, "Design and responses of Butterworth and critically damped digital filters," J Electromyogr Kinesiol. 2003 December;13 (6):569-73).

The following provides a brief mathematical synopsis of the lock-in algorithm 700, as referenced above, and is followed by a unique exploitation of a simple finite impulse response (FIR) low pass filter, according to one embodiment of the invention.

One stipulation imposed on by phase sensitive detection is that the source intensity must be modulated with a sinusoidal waveform. In our instance, this is accomplished by modulating the bias current feeding the laser diode. Say that our input signal for channel j is expressed as $V_{m,j}(t) = A_{m,j} \bullet \sin(2\pi f_m t + \Phi_{m,j})$, where $A_{m,j}$ is the amplitude of the optical signal at detector j, $f_m$ is the source (modulation) frequency, and $\Phi_{m,j}$ is the phase shift. Since we are digitizing this waveform by acquiring $N_s$ samples at frequency $f_s$ hertz (sampling rate), it retains a discretized representation of $V_{m,j}[n] = A_{m,j} \bullet \sin(2\pi f_m n/f_s + \Phi_{m,j})$. Now suppose we have a digitally synthesized reference signal whose format is also an $N_s$ point discrete sequence and is represented by $S_{ref}[n] = A_r \bullet \sin(2\pi f_r n/$ $f_s+\Phi_{ref}$) where $A_r$ is the amplitude of the reference signal, $f_r$ is the reference frequency, and $\Phi_{ref}$ is its respective phase shift. If these two signals are multiplied together, the product consists of multiple elements:

$$V_{m,j} \cdot S_{ref} = A_{m,j}A_r(1/2)\{\cos([2\pi f_m - 2\pi f_r](n/f_s) + \phi_{m,j} - \phi_{ref}) - \cos([2\pi f_m + 2\pi f_r](n/f_s) + \phi_{m,j} + \phi_{ref})\} \quad (5)$$

{using the trigonometric identity; sin u sin v=(½){[ cos(u−v)−cos(u+v)]}

Homodyne (synchronous) detection dictates that the reference frequency must be identical to the source-modulation frequency. Applying this constraint to the above equation yields;

$$I_{m,j}[n]=V_{m,j}\bullet S_{ref}=A_{m,j}A_r(\tfrac{1}{2})\{\cos(\phi_{m,j}-\phi_{ref})-\cos([4\pi f_m(n/f_s)]+\phi_{m,j}+\phi_{ref})\} \quad (6)$$

The two components provide unique frequency contributions to the composite waveform; one is sitting at zero frequency (DC) whose magnitude is proportional to the phase difference between the optical and reference signals, and another component that is positioned at twice the modulation frequency on the Fourier spectrum. By sending the resulting signal through a low-pass filter we suppress the higher frequency component to obtain:

$$X_{m,j}[n]=A_{m,j}A_r(\tfrac{1}{2})\{\cos(\phi_{m,j}-\phi_{ref})\}=A_{m,j}A_r(\tfrac{1}{2})\{\cos(\theta_j)\} \quad (7)$$

The amplitude of the output signal is contingent on the amplitudes of the detected signal, the references signal, and the phase difference between them. If a fixed phase relationship is maintained and doesn't vary over time, then the final DC signal is directly proportional to the input signal. In an effort to maximize the DC value, one would normally be required to incorporate various phase shifting schemes. This problem is compounded in our application because each channel retains a distinctive phase, a consequence of the sampling process. Therefore, employing independent phase shifters would be imposed on the system for each detector channel and each wavelength. In some embodiments, to avoid the complexity of having to integrate many individual phase shifters, a solution is provided that makes use of an additional mixing stage with a quadrature reference signal.

The quadrature lock-in method is an elegant approach with which one can eliminate the phase dependency entirely. To accomplish this, the input signal must also be multiplied by a 90-degree phase-shift of the original reference, $C_{ref}[n]=A_r \bullet \sin(2\pi f_r n/f_s+\Phi_{ref}+\pi/2)$. Similar to the procedure outlined above, when the two signals are mixed and passed through a low-pass filter, we get another phase-contingent association:

$$Q_{m,j}[n]=A_{m,j}\sin(2\pi f_m n/f_s+\Phi_{m,j})\bullet A_r\cos(2\pi f_r n/f_s+\Phi_{ref})$$

$$Y_{m,j}[n]=A_{m,j}A_r(\tfrac{1}{2})\{\sin(\phi_{m,j}-\phi_{ref})\}=A_{m,j}A_r(\tfrac{1}{2})\{\sin(\theta_j)\} \quad (8)$$

If we now calculate the magnitude of the X and Y expressions, we obtain:

$$r_{m,j}^2 = X_{m,j}^2 + Y_{m,j}^2 \quad (9)$$

$$r_{m,j}^2 = SQRT(X_{m,j}^2 + Y_{m,j}^2)$$

$$= SQRT\{[(1/2)A_{m,j}A_r]^2 \cdot [\cos^2(\theta_j)+\sin^2(\theta_j)]\}$$

$$= (1/2)A_{m,j}A_r$$

This method yields a value that is independent of the phase differences and is directly related to the amplitude of channel j.

It is to be noted that, in some embodiments, the lock in detection can be, but is not limited to, a phase-insensitive quadrature method. Digital detection or lock-in techniques employing phase-diversity or phase-dependent detection, with or without utilizing a phase shifter, are also provided in some embodiments of the invention.

Extension of the above technique becomes a little more involved when one incorporates multiple wavelength imaging. Suppose, for example, that have two light sources modulated at f1=3 kHz and f2=5 kHz superimposed on one another. The resulting signal is the sum of the two individuals sinusoids:

$$V_{f1}+V_{f2}=V_1\sin(f_1 t)+V_2\sin(f_2 t) \quad (10)$$

If one multiplies this signal with a single reference signal, say at frequency f1 (3 kHz), the product will consist of multiple components spread out across the frequency spectrum.

f1−f1=0 Hz=DC component  I)

f1+f1=3 kHz+3 kHz=6 kHz  II)

f2−f1=5 kHz−3 kHz=2 kHz  III)

f2+f1=5 kHz+3 kHz=8 kHz  IV)

The only quantity we wish to preserve is the one straddling zero frequency. As has been shown before, this value is directly proportional to the amplitude of the optical input signal. The other frequency components should be eliminated via the low-pass filter. Elimination of the other frequency components can be achieved via a low-pass filter. Effective extraction of a single frequency band while suppressing all others, has direct implications on the bandwidth of the filter chosen and of the spacing between two modulation frequencies to ensure that NONE of the unwanted fractions falls into the passband of the filter.

In some embodiments, the lock-in filter can be an ordinary averaging filter. The following description, which references FIGS. 9-11, relates generally to a digital lock-in amplification scheme that is optimal for lock-in detection and optical imaging, including continuous wave (CW) imaging, according to some embodiments of the invention. In some embodiments, the digital lock-in amplification scheme is for simultaneously measuring amplitude and phase of multiple modulated optical signals used in continuous wave optical imaging. A digital lock-in algorithm according to some embodiments of the invention is described, including being described under certain sampling and modulation conditions, and results are shown for sample data. The detection scheme, after careful choice of sampling and modulation frequencies, can be excellent or ideal for isolating signals modulated by different frequencies. Its filter also provides good or the best non-DC rejection vs. time response characteristics.

Figure 9:
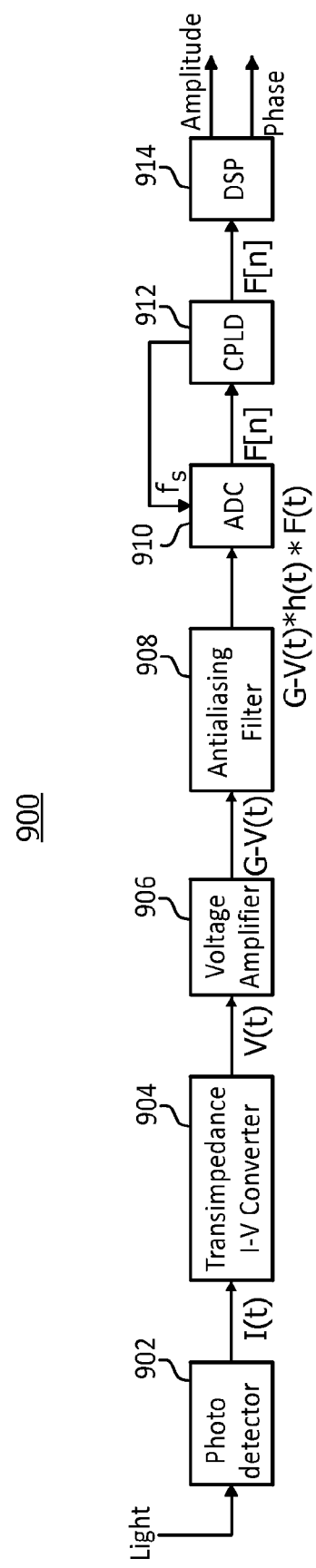
FIG. 9 is a block diagram depicting hardware components of a digital CW instrument, according to one embodiment of the invention.

FIG. 9 is a block diagram depicting hardware components 900 of a digital CW instrument, according to one embodiment of the invention. Photo detector 902 outputs a current signal, I(t), proportional to the incident light signal, which is then converted to a voltage, V(t), by a transimpedance I-V converter 904 and then amplified by a voltage amplifier 906 with gain G. An antialiasing filter 908, h(t), makes sure there are no frequencies above the nyquist frequency. ADC 910 samples the signal, F(t), at a frequency $f_s$ controlled by a CPLD controller 912. The digital signal F[n] is then sent though the CPLD 912 on the way to DSP 914 where the lock-in algorithm, according to some embodiments of the invention, is performed and outputs the amplitude and phase for every modulation frequency.

According to some embodiments, every time an imaging system wants to measure the amplitude and phase of a signal, the lock-in algorithm actually takes $N_s$ samples at sampling frequency $f_s$. This means the data acquisition time is:

$$T_{acq} = N_s/f_s \qquad (11)$$

Since the sampling is controlled by some digital controller with a clock frequency $f_{clk}$. Only certain values of fs are allowed:

$$f_s = f_{clk}/N_c \qquad (12)$$

where $N_c$ is the integer number of clock cycles it takes the digital controller to run through a sampling period.

In some embodiments, in order for the averaging lock-in algorithm to work, the modulation frequency, fm, must be some integer multiple of:

$$T_{acq}^{-1}, f_m = k \cdot f_s/N_s \qquad (13)$$

With these constraints, one can use a simple $N_s$ point averaging filter:

$$g[n] = 1/N_s \qquad (14)$$

to both remove noise and isolate signals. The magnitude response of the averaging filter g[n] has a stopband attenuation of $20*\log(N_s)$ and can be approximated as:

$$|G(f)| = |\sin c(N_s\pi f/2f_s)| \qquad (15)$$

which clearly has zeroes at $f = f_m$.

Instead of a reference signal, in some embodiments, the lock-in algorithm stores an Ns point sequence of $C_m[n] = \cos[2\pi f_m n/f_s]$ and $S_m[n] = \sin[2\pi f_m n/f_s]$, for every modulation frequency $f_m$. If the signal is:

$$F_m(t) = A_m \cos(2\pi f_m t + \phi_m) \qquad (16)$$

then the digital signal is:

(17) $F_m[n] = A_m \cos[2\pi f_m n/fs + \phi_m]$. The first step of the algorithm is to modulate the signal by the stored sequences for every modulation frequency to produce 2 new sequences:

$$I_m[n] = C_m[n] \cdot F[n] = A_m/2 \cdot \cos(\phi_m) + A_m/2 \cdot \cos[4\pi f_m n/f_s + \phi m] \qquad (18)$$

and:

(19) $Q_m[n] = S_m[n] \cdot F[n] = A_m/2 \cdot \cos(\phi_m) + A_m/2 \cdot \sin[4\pi f_m n/f_s + \phi m]$. These sequences are then filtered by averaging filter. This is the same thing as taking the mean of the sequence to result in the following values:

$$X_m = \frac{1}{N}\sum_{n=1}^{N_s} I_m[n], \qquad (20)$$

-continued $$Y_m = \frac{1}{N}\sum_{n=1}^{N_s} Q_m[n]. \qquad (21)$$

By equation (13) one can see that the mean is taken over k complete periods of F[n] and thus when the second non-dc terms in (18) and (19) are averaged over 2 k complete periods the result is zero. What are left are the quadrature components of the amplitude divided by 2 so that the amplitude is:

$$A_m = 2\sqrt{(X_m^2 + Y_m^2)}. \qquad (22)$$

The phase $\phi_m$ is found by taking the quadrant dependent inverse tan function:

$$\varphi_m = -\tan^{-1}\left(\frac{Y_m}{X_m}\right). \qquad (23)$$

It is well known that the optimum filter for white noise suppression and DC retention is the averaging filter [4], but due to careful choice of sampling and modulation frequencies to the constraints in (13), according to some embodiments of the invention, it is also optimum for removing the any signals that are multiples of $f_s/N_s$. When using multiple modulated sources S(t) is actually:

$$F(t) = \sum_m A_m \cos(2\pi f_m t + \varphi_m). \qquad (24)$$

Generally, with other lock-in filters the additional frequency components interfere with accurate measures of $A_m$ and $\phi_m$, but with the digital lock-in filter, according to some embodiments of the invention, these frequencies are zeroed out when averaged after being modulated by a reference sequence which is not of the same frequency. As a proof one can see the following is a consequence of (13) and (15).

$$G(f_i + f_j) = G(f_i - f_j) = 0 \quad (i \neq j). \qquad (25)$$

When signals are modulated together the resulting frequencies are the sum and difference of the two frequencies. If the original frequencies are not the same, the signals at the two new frequencies are zeroed by the averaging filter. This means that a source can be modulated by many frequencies without them interfering with each other.

Figure 10:
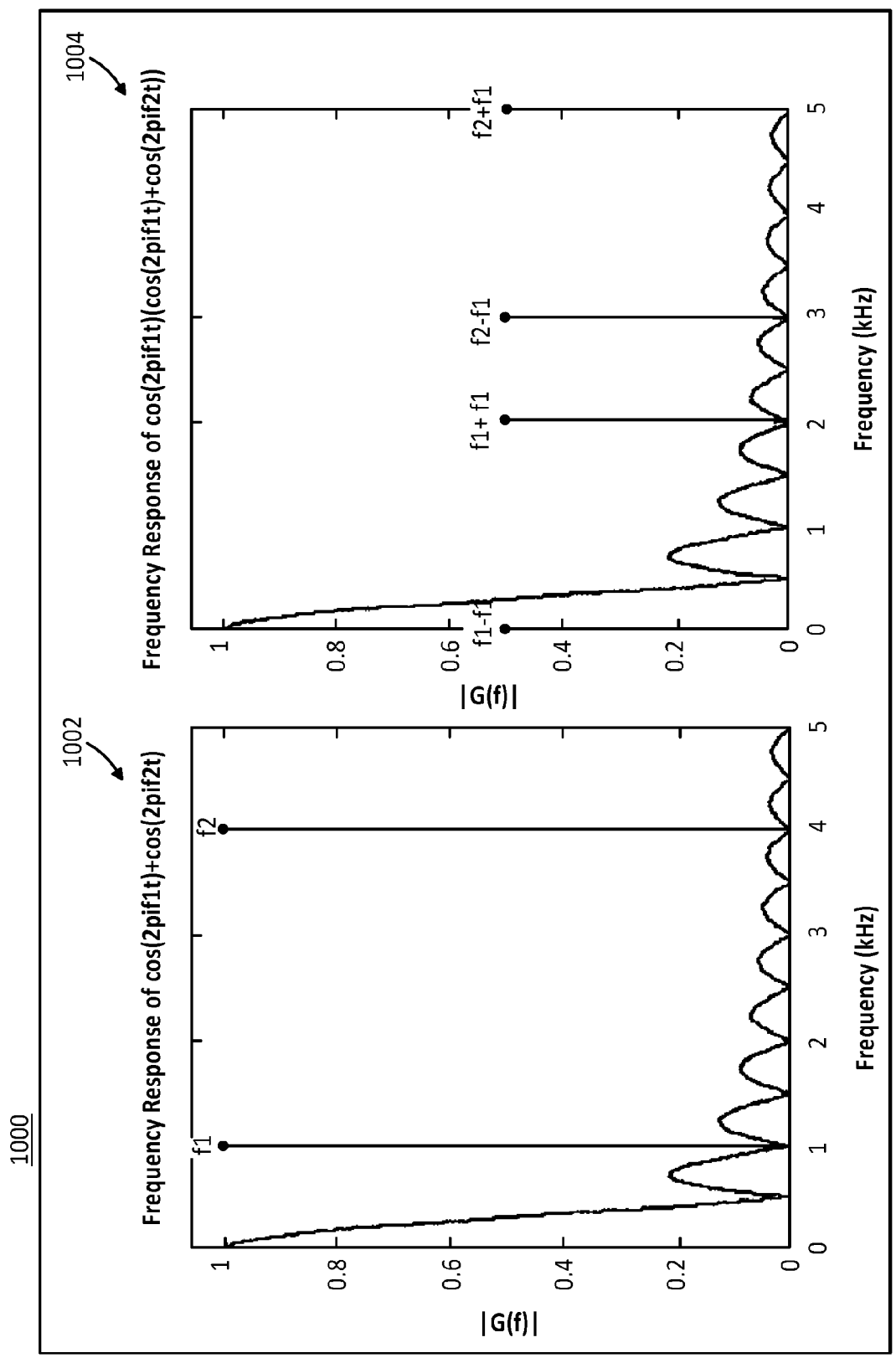
FIG. 10 is a set of graphs depicting frequency response of filter, original, and modulated signals, according to one embodiment of the invention.

FIG. 10 is a set 1000 of graphs 1002, 1004 depicting frequency response of filter, original, and modulated signals, according to one embodiment of the invention. FIG. 10 shows that when a set of modulated signals are modulated by a reference, the only signal that does not fall into a zero bin is when the two signals have the same frequency. When frequencies other than specified are used, inaccurate measures of amplitude and phase result.

Figure 11:
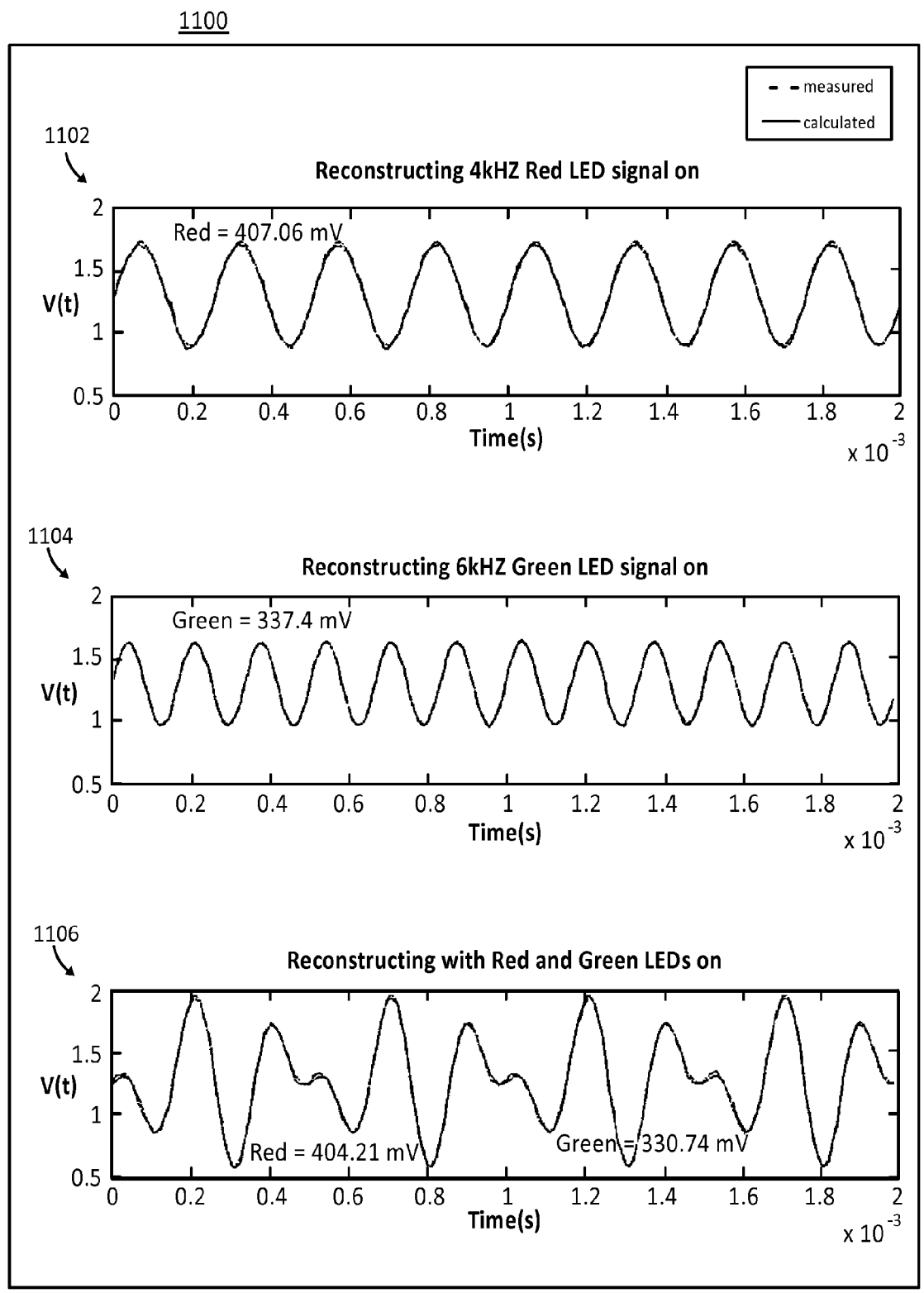
FIG. 11 is a set of graphs that depict plots of calculated signals along with the measured signals, according to one embodiment of the invention.

The following, including the description with reference to FIG. 11, relates to results of testing of a lock-in algorithm, according to some embodiments of the invention, on measurements. Red and green LED's were modulated in a very noisy environment by 4 kHz and 6 kHz wave respectively and the shown onto a single photo detector, such as the photodetector 902 depicted in FIG. 9. For convenience analog signals where sampled with an oscilloscope after the filter stage in FIG. 9. Data was saved to a disk and the algorithm was performed using MATLAB. The amplitudes of the signals were kept at a constant value or turned off completely. Measurements were taken with just the red LED on, just the green LED on, and both of them on. The calculated amplitude and phase were used to reconstruct the measured signals in order to verify that the results were correct.

FIG. 11 depicts a set 1100 of graphs 1102, 1104, 1106 that depict plots of these calculated signals, as described above, along with the measured signals. The graphs 1102, 1104, 1106 depict measured signals, calculated amplitudes, and reconstructed signals. Calculated amplitudes are shown by each plot.

It is to be noted that, with reference to FIGS. 9-11, while techniques are described primarily with reference to CW imaging, they can also be extended into the frequency domain.

The following provides description relating to circuit construction and signal conditioning to accommodate desired bandwidth, sensitivity, and temporal response, with regard to embedded digital signal processing techniques used in optical tomography.

Numerous methods are currently used to collect and analyze light transmission data in optical tomographic imaging studies. The processes are categorized as time domain, frequency domain, and steady-state or CW domain. These techniques differ in the temporal characteristics of the illuminating source and hence their respective detection techniques. Each approach features unique benefits and deficiencies. Examples of instruments utilizing the various methods as well as advantages and disadvantages of the different approaches have been described in literature. Although the steady-state approach provides data with the least information content, it provides many benefits related to cost/performance issues.

Existing instruments used to generate optical measurements utilize an analog scheme to collect, condition, and filter the incident signal. On some systems, analog phase-sensitive lock-in methods are employed to extricate the optical signal obscured by noise of potentially greater magnitude. Such analog detection systems, however, suffer from a number of deficiencies and limitations. More specifically, analog phase sensitive detection has many problems associated with it that adversely affect their performance and restrict subsequent applications. Some primary deficiencies include signal drift, output offsets, gain error, limited dynamic reserve, and harmonic rejection. Additionally, external parameters such as temperature or age contribute to analog noise and, consequently, measurement uncertainty. Furthermore, analog processing is notably sensitive to component tolerances thereby limiting functional utility. Finally, when the digital timing signals share a backplane with analog data signals, coupling can occur causing fluctuations along the analog lines. Consequently, the instrument noise floor is elevated, sensitivity is reduced, and dynamic range is diminished.

The architecture introduced herein, according to some embodiments of the invention, provides a versatile, compact, high precision optical-measurement system by applying integrated digital data acquisition and digital signal processing techniques. In general, digital-based systems offer distinct functional benefits over their analog counterpart including noise reduction, maintaining signal integrity, and enhancing overall performance. Additionally, a detection device, according to some embodiments of the invention, unlike existing digital systems, implements the data-acquisition and filtering via a signal processor embedded in-system conserving costs, reducing power and size, increasing speed, and generating real-time measurements. The circuitry was fashioned for swift data transfers and a settling time reduction of both the analog front-end electronics, and the digital filter compared to the former system. This affords faster source-switching speeds, yielding high acquisition rates which facilitate the study of functional imaging.

Figure 12:
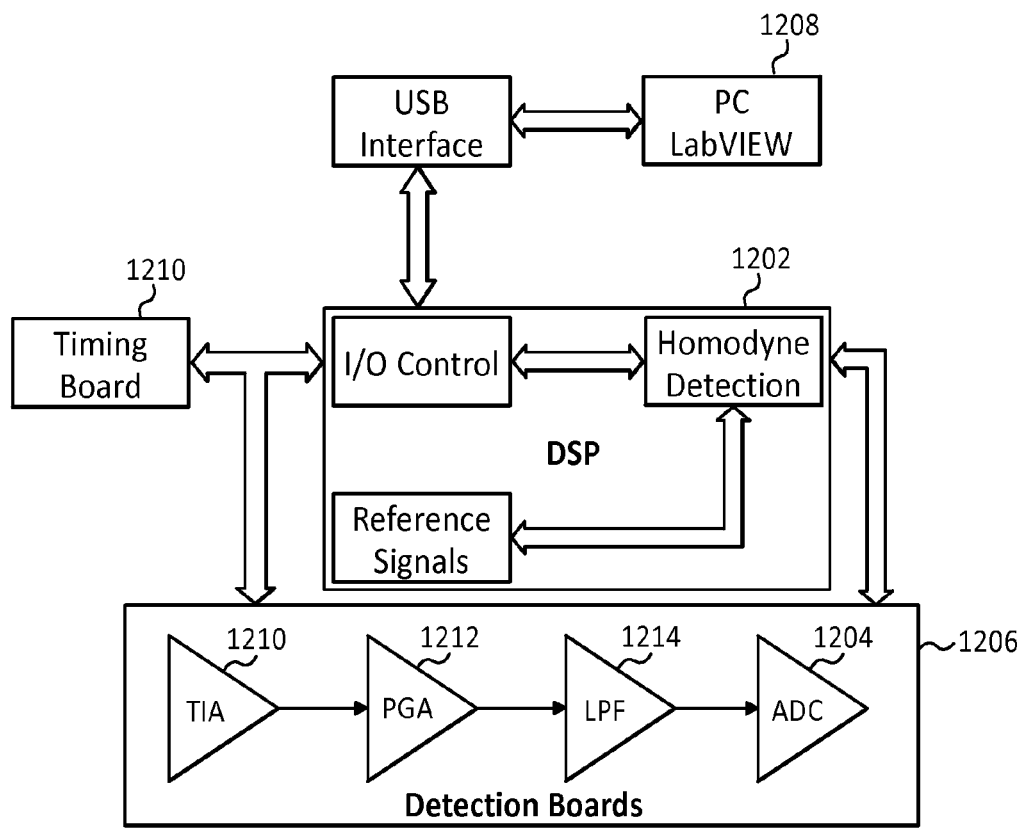
FIG. 12 is a block diagram depicting system layout and signal communication, according to one embodiment of the invention.

FIG. 12 is a block diagram 1200 depicting system layout and signal communication, according to one embodiment of the invention. DSP 1202 is the component by which the signals are collected, processed and filtered, and finally routed to a host PC 1208. In some embodiments, the system uses Model ADSP-21161 with Super Harvard Architecture Computer (SHARC), available from Analog Devices, Inc., whose key features include 600 MFLOPS peak, 32-bit and 40-bit floating point arithmetic and user-configurable 1 MBits on-chip SRAM memory. The system employs parallel detection to assist in achieving a high temporal resolution. The design accepts up to 32 independent detectors simultaneously whose distribution comprises 8 Printed Circuit Boards (PCB), each accommodating 4 channels. A single 4-channel high-speed 16-bit Analog to-Digital Converter (ADC) 1204 is mounted on each board 1206. A timing board 1210 consisting of the Complex Programmable Logic Device (CPLD), clock, and some support circuitry is interfaced with the DSP 1202 and detector boards 1206. The USB protocol is used to transfer data between the DSP 1202 and the host PC 1208. The USB chip with its support circuitry and interface glue logic is mounted on a separate PCB.

In some embodiments, the photodiode and trans-impedance amplifier 1210 of the system of FIG. 12 are similar to those of the system described in Schmitz 2002. Silicone-based photodiodes provide the sensitivity, frequency response, and linearity requisite for the application. These attributes combined with their low cost and low dark current make them optimal for the design.

The trans-impedance amplifier (TIA) 1210 was carefully selected to keep the existing and inherent noise minimal. The feedback network of the TIA 1210 and a subsequent PGA 1212 stage offer a multitude of signal gain stages to provide a large global dynamic range for each channel and to maximize the resolution of the 16-bit ADC. A gain of 1, 10, or 10,000 kV/A is available from the TIA 1210 feedback while an additional gain of 1, 10, or 100 V/V is offered by the PGA yielding a dynamic range exceeding 120 dB and an absolute maximum signal gain of $10^9$ V/A (180 dB). A 16-bit ADC offers up to 0.0015% resolution full-scale, so the system can theoretically detect 0.76% fluctuations for signals as small as 10 pA, the approximate noise floor.

In some embodiments, before the analog signal can be digitized, it must be sent through a low-pass anti-aliasing filter 1214 so that the frequency spectrum conforms to the Nyquist limitation. Since the sampling rate is ~75 k samples/sec and the modulation frequencies of the lasers are from 1-9 kHz, the filter's impulse response can be enhanced at the expense of the frequency roll-off. The filter chosen is an 8th order Butterworth, which afford a balance between the time versus frequency response tradeoff. With a cutoff frequency of 12.5 kHz, one achieves 0.1% attenuation at the upper limit of modulation (9 kHz). By sampling at 75 ksps, noise above 67 kHz can alias into the passband. However, the filter attenuation at this frequency is −117 dB which is adequate noise suppression. An impulse at the input of the LPF yields a filter settling time of 450 μsec, not a limiting factor in the general detection temporal response. Once the signal is filtered, it is digitized by a 16-bit SAR (Succession Approximation Register) Analog-to-Digital Converter 1204. The ADC has a 4-channel multiplexed input and a serial output which directly interfaces with the DSP 1202. Its maximum sampling rate of 1 Msps assures that every channel is sampled at the desired 75 ksps.

The detection scheme assumes an amplitude-modulated light source, which allows one to execute the lock-in operation. In some embodiments, by transferring the lock-in detection from the analog to the digital (software) domain, the offset errors, nonlinearities, and drifts are greatly reduced or virtually eliminated. As stated above, the digitized data signals from all detectors are time-division-multiplexed onto a double serial line. Once the DSP 1202 receives the data from the ADC 1204, it collates the signals and performs the homodyne detection algorithm. This technique mixes the optical signal with a DSP-generated reference signal at an identical frequency and sends the output through a low-pass filter. The result is a DC signal whose magnitude is proportional to magnitudes of the optical power and reference voltage, and their phase difference. By mixing the original signal with both the in-phase and quadrature components of the reference, the final output is independent of phase difference and is only contingent on the amplitude of the inputs. In some embodiments, this is an attractive option for some systems as described herein, for example, since all channels do not share a common phase, an effect of the sampling sequence. The homodyne algorithm can be easily extended to accommodate multiple wavelengths, and the low-pass-filter 1214 is specifically designed with this consideration.

In the embodiment depicted in FIG. 12, a low-pass filter 1214 used for the lock-in stage is an ordinary averaging filter; however, in other embodiments, other filters may be used. By carefully choosing the sampling frequency, modulation frequencies and the number of samples acquired, the unique frequency response of this filter type can be exploited. Analysis and investigation of the filter's magnitude response, which is $|H(jw)|=\sin c(N_s w/2 f_s)$, where $j=\sqrt{-1}$ and w is the angular frequency, reveals particular frequencies throughout the spectrum that are zeroed out. The relationship between these eliminated frequencies, sampling frequency, modulation frequencies, and number of samples is as follows.

$$f_{zero}=k[f_{Nyquist}/(N_s/2)]=k[f_s/(N_s)], f_m=f_{zero} \quad (26)$$

Where N is the number of samples acquired, k is any positive integer, $f_{Nyquist}=f_s/2$, and $f_m$ is the modulation frequency. $f_s$ and $N_s$ are chosen based on based on various resulting tradeoffs.

It is instructive to note practical and constructive consequences arising by adhering to the above correlations. Firstly, k complete periods are always accumulated at that particular modulation frequency. This fact can be demonstrated by the following relationships:

$$T_m=T_{zero}=[(N_s/k)T_s], T_{acq}=N_s T_s, \text{ so } T_m=T_{acq}/k \text{ or } T_{acq}/T_m=k \quad (27)$$

Where $T_{acq}$ is he data acquisition period for a single channel, and $T_x$ is the period of parameter x. Secondly and significantly, the product of the detected light signal (with multiple modulation frequencies/wavelengths) and a single reference signal results in the cancellation of all additive frequency components except the one being "locked onto" which sits at DC. This is a significant motivation for employing the averaging filter for the application.

Figure 13:
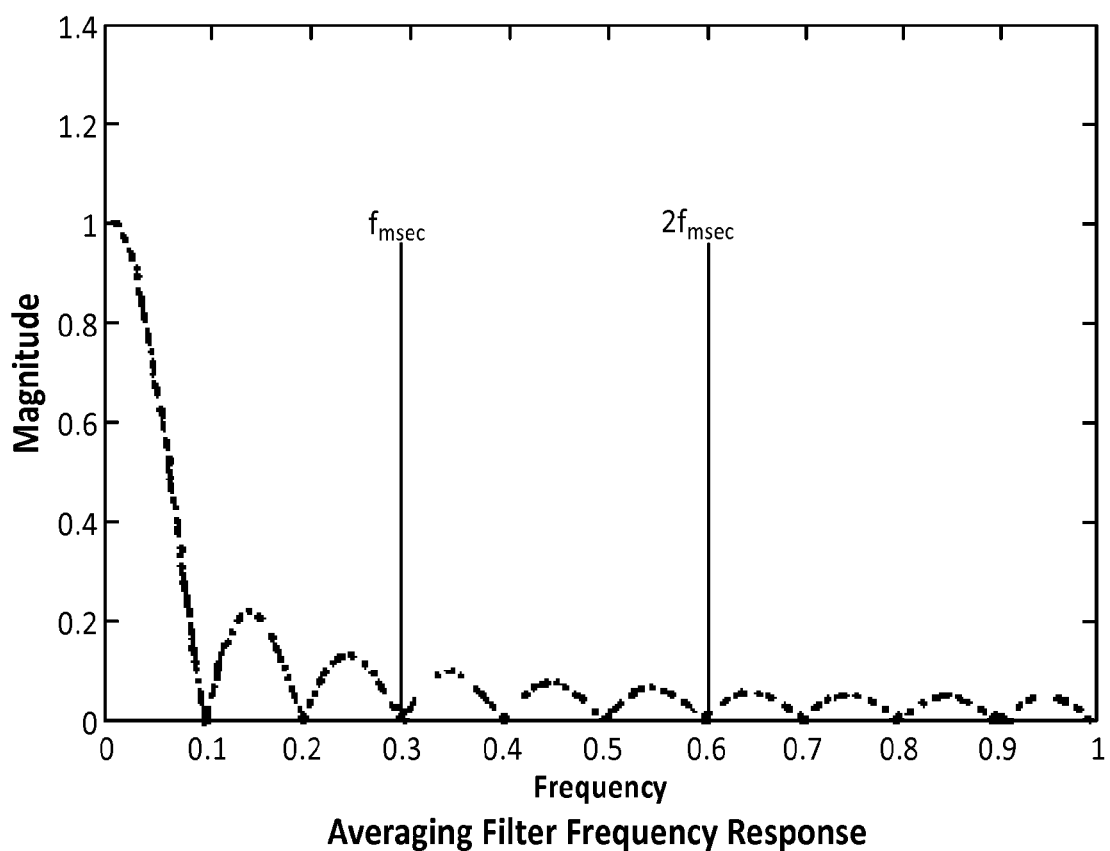
FIG. 13 is a graph 1300 depicting frequency response of a 20 point averaging filter, with the horizontal frequency axis running from zero to Nyquist frequency.

FIG. 13 is a graph 1300 depicting frequency response of a 20 point averaging filter, with the horizontal frequency axis running from zero to Nyquist frequency.

With respect to collecting data, once the DSP has completed its calculation, the data must be streamlined into the host computer. In some embodiments, because the DSP has many responsibilities and processes accessing its data busses and internal memory, immediately after performing the lock-in computations the DSP deposits the data values in an external memory bank. There, it can be accessed by a timed transfer protocol and directed to the host PC without causing a bottleneck in the digital processor. Furthermore, data latches and control circuitry are used to coordinate the gain-bits being downloaded from the host PC into the signal processor. To properly buffer the data transfers, bi-directional driver and transceiver devices are implemented to all data transmissions. Streamlining measurement results or gain-bit values can be accomplished via a microcontroller-based USB protocol. USB offer many distinct benefits, making it the interface-bus of choice. It makes the instrument portable, eliminates the need for a data-acquisition board, presents a plug-and-play design, and can support transfer speeds up to 480 Mb/s. This electrically simple user experience requires some inner complexity and adds a whole protocol layer to the system interface. LabVIEW is the PC control software, available from National Instruments Corp., which integrates embedded C-code to communicate with the USB's microcontroller. The timing sequences required for data transfers between the host PC and embedded DSP are synchronized by a designated controller or programmable logic device.

One of the major challenges to the system's design is orchestrating the multitude of events transpiring for each imaging frame. For every source position, the gain bits must be updated for each detector channel and the settling time of the optical switch and the analog electronics must be obeyed. The sampling of the detectors must be synchronized meticulously so they can be efficiently streamlined into the DSP 1202 in a time-division multiplexed fashion. The complexity is recognized by the realization that the objective is to multiplex 32 channels, 200 samples/channel, and 16 bits/sample into a single serial port in 2 msec. These functions are executed by a high-performance Complex Programmable Logic Device (CPLD). This device acts as a multi-level state machine, and can simulate a variety of standard logic operations. Among other functions, during the imaging routine the CPLD is responsible for triggering the sampling process of the ADC's and for sequentially accessing the digitized data so that it can be time-division multiplexed into the DSP.

Generally, in some embodiments, lock-in detection is performed through software algorithms, enhancing signal integrity by eliminating the analog shortcomings, and making it configurable to the user's specific application. In some embodiments, by adhering to the techniques and circuit construction reviewed herein, the resulting instrument eliminates many adverse analog affects and offer greater functionality than related systems.

In some embodiments, the invention provides systems, methods, and apparatuses associated with an illuminating source for a digital optical imager, such as a digital optical imager usable in optical tomography. In some embodiments, these methods, systems, and apparatuses can be used, for example, with systems and methods described previously herein, including, for example, the system 200 depicted in FIG. 2, as described in detail above.

Figure 14:
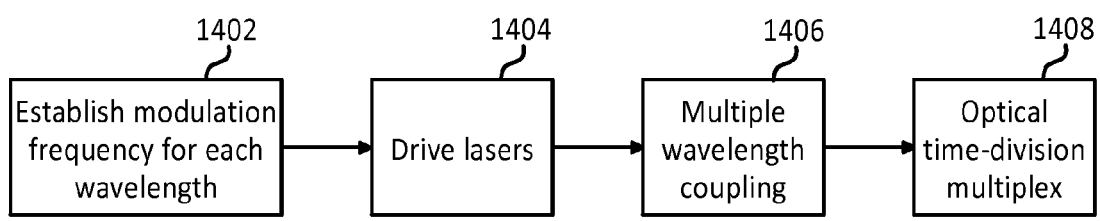
FIG. 14 is a flow diagram depicting a method 1400 according to one embodiment of the invention.

FIG. 14 is a flow diagram depicting a method 1400 according to one embodiment of the invention, for generating multi-wavelength illuminating sources at multiple locales, as required for attaining spectroscopic tomography.

Step 1402 includes establishing modulation frequency for each wavelength.

Step 1404 includes driving lasers.

Step 1404 includes performing multiple wavelength coupling.

Step 1406 includes optical time-division multiplexing.

In some embodiments, since a phase sensitive detection scheme is employed to extract the amplitude of the optical signal, it is required to amplitude-modulate the light source that probes the tissue and provide a reference frequency equal to and phase-locked with the modulation frequency. When using multiple wavelengths simultaneously, each requires their own distinct modulation frequency to encode the optical intensity and reference signals to decode it.

In some embodiments, to generate a modulation frequency, direct digital synthesis (DDS) technology is used. Direct digital synthesis is a method of producing an analog sine waveform by generating a time-varying signal in digital form and then performing a digital-to-analog conversion. Because operations within a DDS device are primarily digital, it can offer fast switching between output frequencies, fine frequency resolution, and operation over a broad spectrum of frequencies. With advances in design and process technology, modern day DDS devices are very compact and consume little power. It therefore serves as a stable and accurate waveform generator to produce the frequency stimulus required for the application. Each DDS device outputs one frequency and therefore supplies only a single illuminating wavelength.

In some embodiments, the design uses a synthesizer that provides two sine waves, in-phase and quadrature, which are 90 degrees phase shifted from each other. This provides the option of sampling both components to use as the reference signals in quadrature lock-in detection, as described in detail above. In some embodiments, the first choice is to digitally generate these reference signals internally in the DSP thereby utilizing the DDS synthesizers only to modulate the lasers. In some embodiments, however, other options may be utilized, such as digitizing the analog reference waveforms instead.

In some embodiments, the DDS contains dual integrated 12-bit digital-to-analog (DAC) converters for high resolution waveforms and demonstrates excellent dynamic performance. A lowpass filter is applied to the produced waveform in an effort to lower the harmonic content even further and make efficient use of the higher precision 16-bit analog-to-digital converters (ADC) used for sampling the detector channels.

In some embodiments, the function of the digital synthesizer is determined and controlled through a set of register values together with specified commands. A designated microcontroller is assigned to interfacing directly with the DDS chips. Programming the relevant instructions required for generating specific waveforms as well as timing organization will be executed via this controller and/or the digital signal processor. Selecting the modulation frequencies can be preprogrammed into the controller or modified spontaneously through computer software or autonomous devices, for example.

Some embodiments provide an instrument that uses laser diodes in the near-infrared region as the radiative source for optical imaging. The lasers are regulated by select OEM laser diode controllers that combine a low noise, low drift current source with a precise thermoelectric cooler (TEC). Operating in constant current mode creates a laser output whose power is proportional to the driving current. Therefore, once the respective frequencies are generated, one can use them to modulate the driving current of the light source, which in effect, modulates the laser output.

In an effort to quantify hemoglobin parameters and other biological chromophores, light transmission data must be collected on multiple wavelengths. The minimum number of wavelengths for performing spectral analysis is two. By combining these wavelengths together and making simultaneous measurements, one can shorten the data acquisition period and increase the temporal response of the instrument. To accomplish this, according to some embodiments, one can use either an independent optical coupler which effectively merges the light from multiple wavelengths or by means of discrete geometric optics components such as beam splitters and/or dichroic mirrors.

In some embodiments, once the light source is modulated, controlled, driven, and combined, the all that's left is to spatially encode multiple illumination locales around the target being probed. A method frequently employed to separate source locations is through time-division multiplexing of the combined light source. This can be realized by a 1×N optical switch where N is the number of different source positions. A single input is routed to a distinct output which is controlled by a specific address. When the switch receives an appropriate address, the input is aligned with the respective output. The settling time of the switch is on the order of 2-5 msec (a significant feature for acquiring dynamic images).

A problem with commercially available switches is that the inter-channel crosstalk is only specified to about −50 to −60 dB while the dynamic range of the instrument is effectively around 90 dB of optical power (when comparably adjusted). This means that light can leak from one channel to another contaminating the measured quantity. To solve this problem, according to some embodiments, one uses a configuration of a 1×N switch in series with a 2×2 optical switch that suppresses crosstalk by over −100 dB.

Figure 15:
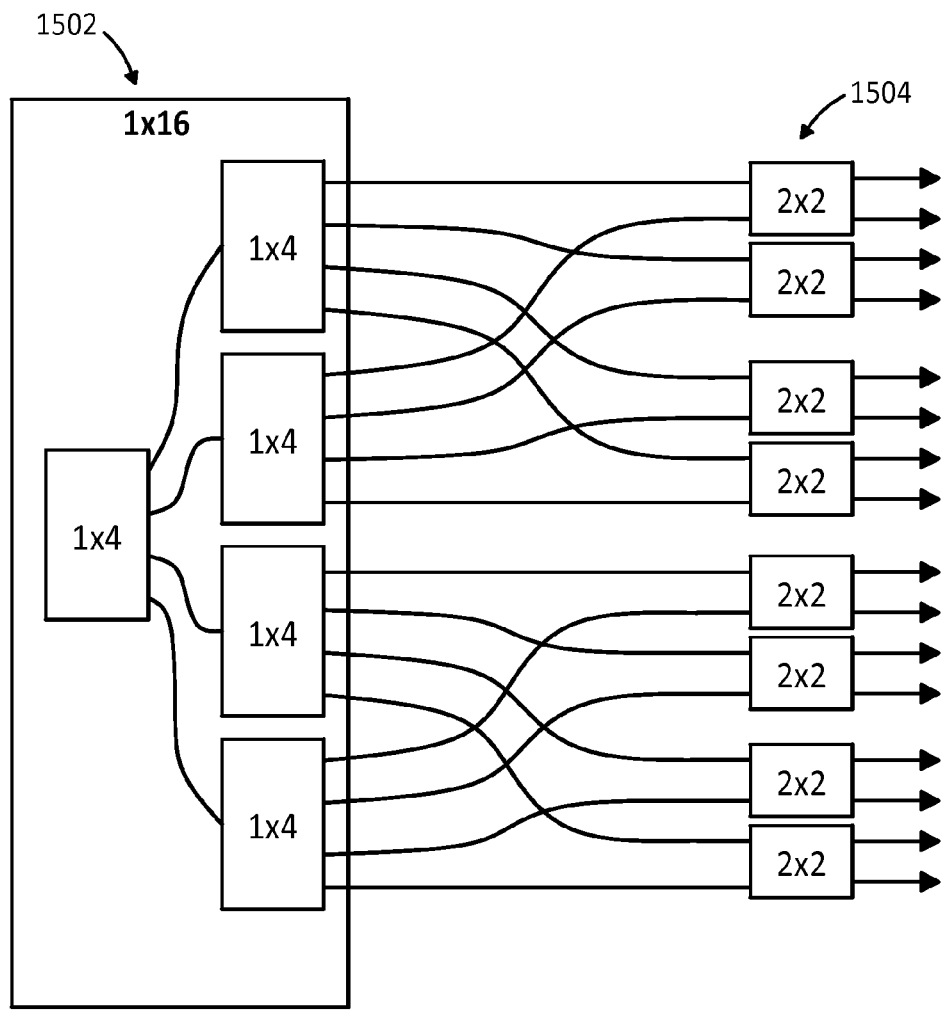
FIG. 15 is a block diagram depicting an optical switch, according to one embodiment of the invention.

FIG. 15 depicts one embodiment of such a configuration. Specifically, FIG. 15 is a block diagram 1500 depicting a 1×16 optical switch 1502 in series with 8-2×2 switches 1504 to provide a composite 1×16 multiplexed source architecture with an effective crosstalk elimination of over 100 dB. As such, in some embodiments, a fast optical 1×N optical switch (N=number of output source positions) with switching time on the order of 2-5 msec can be utilized to achieve over 100 dB of crosstalk isolation by judiciously cascading multiple switching stages.

In some embodiments, the output of the optical switch then interfaces directly with the tissue or measurement probe. This entire apparatus can function independently or be controlled by a personal computer, for example. Offering variable parameter control will allow for spontaneous user command. Also, an LCD display may be integrated into this setup to provide the user with some system monitoring and feedback.

What is claimed is:

1. A digital detection method for use in diffuse optical tomography, the method comprising:

obtaining an analog signal modulated to contain diffuse optical tomographic information by directing a light source at an object and detecting the attenuated light exiting the object;

converting the analog signal into a digital signal; and performing digital processing and lock-in detection on the digital signal using an embedded digital signal processor-based detection module that includes a controller or programmable logic device to facilitate obtaining the diffuse optical tomographic information from the digital signal; and transmitting the obtained diffuse optical tomographic information in digital form to a host computer for display and storage.

2. The method of claim 1, wherein the object is one or more of a tissue, an organ, and a limb.

3. The method of claim 1, comprising obtaining an analog signal amplitude-modulated to contain diffuse optical tomographic information.

4. The method of claim 1, comprising obtaining the analog signal by using a photo-detector to convert light energy into an electronic representation.

5. The method of claim 1, comprising, prior to converting the analog signal into the digital signal, amplifying the analog signal.

6. The method of claim 1, comprising, prior to converting the analog signal into a digital signal, passing the analog signal through a low-pass anti-aliasing filter.

7. The method of claim 1, comprising converting the analog signal into a digital signal using an analog to digital converter.

8. The method of claim 1, comprising converting the analog signal into the digital signal immediately following programmable gain amplification.

9. The method of claim 1, wherein performing digital lock-in detection comprises performing homodyne detection to extricate desired frequencies from noise of greater frequency than the desired frequencies.

10. The method of claim 1, wherein the embedded digital signal processor-based detection module is integrated into detection electronics as a single system.

11. The method of claim 1, comprising storing the digital output from the embedded digital signal processor-based detection module in a database.

12. The method of claim 1, wherein performing digital processing and lock-in detection comprises performing digital filtering with specific sampling constraints that optimize an averaging filter for source discrimination.

13. The method of claim 1, wherein digital lock-in detection is performed using a lock-in algorithm.

14. The method of claim 13, wherein digital lock-in detection is performed using a phase-independent quadrature technique which eliminates phase dependency in lock-in detection.

15. The method of claim 1, comprising detecting multiple wavelengths in parallel.

16. A digital detection method for use in diffuse optical tomography, the method comprising:
   obtaining an analog signal modulated to contain diffuse optical tomographic information;
   amplifying the analog signal;
   filtering the amplified analog signal using a low-pass filter;
   converting the filtered analog signal into a digital signal;
   performing digital processing and lock-in detection on the digital signal using an embedded digital signal processor-based detection module that includes a controller or programmable logic device to facilitate obtaining the diffuse optical tomographic information from the digital signal; and
   transmitting the obtained diffuse optical tomographic information in digital form to a host computer for display and storage.

17. A digital detection method for use in diffuse optical tomography, the method comprising:
   obtaining an analog signal modulated to contain diffuse optical tomographic information;
   amplifying the analog signal;
   filtering the amplified analog signal using a low-pass filter;
   converting the filtered analog signal into a digital signal;
   performing digital processing and lock-in detection on the digital signal using an embedded digital signal processor-based detection module that includes a controller or programmable logic device to facilitate obtaining the diffuse optical tomographic information from the digital signal; and
   transmitting the obtained diffuse optical tomographic information in digital form to a host computer for display and storage,
   wherein performing digital lock-in detection comprises using a lock-in algorithm employing a phase-independent quadrature technique with specific sampling constraints that optimize an averaging filter for source discrimination.

18. A digital detection system for use in diffuse optical tomography, the system comprising:
   a low-pass anti-aliasing filter;
   an analog to digital converter; and
   an embedded digital signal processor-based detection module that includes a controller or programmable logic device;
   wherein an analog signal modulated to contain diffuse optical tomographic information is input to the low pass filter to obtain a filtered output analog signal;
   wherein the filtered output analog signal is input to the analog to digital converter to be converted into an output digital signal;
   wherein the output digital signal is input to the embedded digital signal processor-based detection module to perform digital processing and lock-in detection on the digital signal to facilitate obtaining the diffuse optical tomographic information from the digital signal; and
   wherein the obtained diffuse optical tomographic information is transmitted in digital form to a host computer for display and storage.

19. The system of claim 18, wherein the analog signal is an amplified analog signal.

20. A digital detection system for use in diffuse optical tomography, the system comprising:
   a trans-impedance amplifier;
   a programmable gain amplifier;
   a low-pass anti-aliasing filter;
   an analog to digital converter; and
   an embedded digital signal processor-based detection module that includes a controller or programmable logic device;
   wherein an analog signal modulated to contain diffuse optical tomographic information is input to the trans-impedance amplifier for amplification to obtain a first output amplified analog signal;
   wherein the first output amplified analog signal is input to the programmable gain amplifier for amplification to obtain a second output amplified analog signal;
   wherein the second output amplified analog signal is input to the low pass filter to obtain a filtered output analog signal;
   wherein the filtered output analog signal is input to the analog to digital converter to be converted into an output digital signal;
   wherein the output digital signal is input to the embedded digital signal processor-based detection module to perform digital processing and lock-in detection on the digital signal to facilitate obtaining the diffuse optical tomographic information from the digital signal; and
   wherein the obtained diffuse optical tomographic information is transmitted in digital form to a host computer for display and storage.

21. The system of claim 20, wherein the system is included in a single integrated instrument, and wherein the embedded digital signal processor-based detection module is implemented in the instrument.

22. The system of claim 20, wherein the programmable logic device at least partially controls system timing.

23. The system of claim 20, comprising a transducer, wherein a diffuse optical signal is converted to the analog signal using the transducer.

24. The system of claim 20, comprising an electronic storage device, wherein the obtained diffuse optical tomographic information is stored in the electronic storage device.

25. The system of claim 24, wherein the diffuse optical tomographic information is stored in a database stored in the electronic storage device.

26. An apparatus for use in diffuse optical tomography, the apparatus comprising:
   a low-pass anti-aliasing filter;
   an analog to digital converter; and
   an embedded digital signal processor-based detection module that includes a controller or programmable logic device;
      wherein an analog signal modulated to contain diffuse tomographic information is input to the low pass anti-aliasing filter to obtain a filtered output analog signal;
      wherein the filtered output analog signal is input to the analog to digital converter to be converted into an output digital signal;
      wherein the output digital signal is input to the embedded digital signal processor-based detection module to perform digital processing and lock-in detection on the digital signal to facilitate obtaining the diffuse optical tomographic information from the digital signal; and
      wherein the obtained diffuse optical tomographic information is transmitted in digital form to a host computer for display and storage.

27. The apparatus of claim 26, wherein the apparatus is integrated in a single instrument.

28. An apparatus for use in diffuse optical tomography, the apparatus comprising:
   a trans-impedance amplifier;
   a programmable gain amplifier;
   a low-pass anti-aliasing filter;
   an analog to digital converter; and
   an embedded digital signal processor-based detection module that includes a controller or programmable logic device;
      wherein an analog signal modulated to contain diffuse tomographic information is input to the trans-impedance amplifier for amplification to obtain a first output amplified analog signal;
      wherein the first output amplified analog signal is input to the programmable gain amplifier for amplification to obtain a second output amplified analog signal;
      wherein the second output amplified analog signal is input to the low pass filter to obtain a filtered output analog signal;
      wherein the filtered output analog signal is input to the analog to digital converter to be converted into an output digital signal;
      wherein the output digital signal is input to the embedded digital signal processor-based detection module to perform digital processing and lock-in detection on the digital signal to facilitate obtaining the diffuse optical tomographic information from the digital signal; and
      wherein the obtained diffuse optical tomographic information is transmitted in digital form to a host computer for display and storage.

29. The apparatus of claim 28, wherein the apparatus is integrated in a single instrument.

30. An apparatus for use in diffuse optical tomography, the apparatus comprising:
   a low-pass anti-aliasing filter for receiving an analog signal modulated to contain diffuse optical tomographic information, and for filtering the analog signal to generate a filtered analog signal;
   an analog to digital converter, communicatively connected to the low-pass anti-aliasing filter, for receiving the filtered analog signal, and for converting the filtered analog signal into a digital signal; and
   an embedded digital signal processor-based detection module that includes a controller or programmable logic device, communicatively connected to the analog to digital converter, for receiving the digital signal, for performing digital processing and lock-in detection on the digital signal to facilitate obtaining the diffuse optical tomographic information from the digital signal, and for transmitting the obtained diffuse optical tomographic information in digital form to a host computer for display and storage.

31. The apparatus of claim 30, wherein the apparatus is integrated in a single instrument.

32. An apparatus for use in diffuse optical tomography, the apparatus comprising:
   a trans-impedance amplifier for receiving an analog signal modulated to contain diffuse optical tomographic information, and for amplifying the analog signal to generate a first amplified analog signal;
   a programmable gain amplifier, communicatively connected to the trans-impedance amplifier, for receiving the first amplified analog signal, and for amplifying the first amplified analog signal to generate a second amplified analog signal;
   a low-pass anti-aliasing filter, communicatively connected to the programmable gain amplifier, for receiving the second amplified analog signal, and for filtering the second amplified analog signal to generate a filtered analog signal;
   an analog to digital converter, communicatively connected to the low-pass anti-aliasing filter, for receiving the filtered analog signal, and for converting the filtered analog signal into a digital signal; and
   an embedded digital signal processor-based detection module that includes a controller or programmable logic device, communicatively connected to the analog to digital converter, for receiving the digital signal, for performing digital processing and lock-in detection on the digital signal to facilitate obtaining the diffuse optical tomographic information from the digital signal, and for transmitting the obtained diffuse optical tomographic information in digital form to a host computer for display and storage.

33. The apparatus of claim 32, wherein the apparatus is integrated in a single instrument.

34. The apparatus of claim 32, wherein the controller or programmable logic device synchronizes a sampling process.

35. The apparatus of claim 32, wherein the controller or programmable logic device synchronizes data transfer sequences from the analog to digital converter to the digital signal processor.

36. The apparatus of claim 32, wherein the controller or programmable logic device establishes communication protocol with the embedded digital signal processor-based detection module to execute functional routines and schedules.

37. The apparatus of claim 32, wherein the controller or programmable logic device, or the digital signal processor, manages illumination sequencing and illumination advancements.

38. The apparatus of claim 32, wherein the controller or programmable logic device, or the digital signal processor, coordinates, directs and manages a data acquisition process.

39. The apparatus of claim 32, comprising switches and multiplexers, and wherein data bits that encode signal amplification settings are decoded by at least some of the switches and the multiplexers.

40. The apparatus of claim 32, comprising detector boards and local memory banks located on at least some of the detector boards, and wherein gain-bits are stored in the local memory banks located on the detector boards.

41. The apparatus of claim 32, comprising a digital synthesizer for generating modulation frequencies.

42. The apparatus of claim 32, wherein digital synthesis is managed and programmed by the controller or the programmable logic device, or the digital signal processor.

43. The apparatus of claim 32, comprising a fast optical 1×N optical switch, wherein N=number of output source positions, with switching time on the order of 2-5 msec and that achieves over 100 dB of crosstalk isolation by appropriately cascading multiple switching stages.

44. The apparatus of claim 32, wherein the host computer is communicatively connected to the embedded digital signal processor-based detection module, and wherein USB transfer protocol is employed to transfer data between the host computer and the embedded digital signal processor-based detection module.

45. The apparatus of claim 44, wherein the host computer is a personal computer.

46. The apparatus of claim 32, wherein the embedded digital signal processor-based detection module is communicatively connected to the host computer and a dedicated timing device, and wherein the dedicated timing device is for assisting in data transfer between the host computer and the embedded digital signal processor-based detection module.

47. The apparatus of claim 32, wherein the embedded digital signal processor-based detection module is communicatively connected to the host computer, bi-directional drivers and transceivers, and wherein the bi-directional drivers and the transceivers are for buffering and driving data being transferred between the host computer and the embedded digital signal processor-based detection module.

48. The apparatus of claim 32, wherein the host computer is communicatively connected to the embedded digital signal processor-based detection module, and wherein the embedded digital signal processor-based detection module includes temporary memory banks into which data output from the digital signal processor can be temporarily deposited until retrieved by transfer protocol to be sent to the host computer.

49. The apparatus of claim 32, wherein the embedded digital signal processor-based detection module is for use in storing and uploading gain-bit values to detector channels of the detector.

50. The apparatus of claim 32, further comprising detector boards, wherein the controller or programmable logic device is for efficiently distributing gain-bits to the detector boards.

51. The apparatus of claim 32, further comprising a CompactPCI-type power supply and on-board regulators, wherein the CompactPCI-type power supply in conjunction with the on-board regulators are for providing necessary power for the embedded digital signal processor-based detection module.

* * * * *

UNITED STATES PATENT AND TRADEMARK OFFICE
CERTIFICATE OF CORRECTION

| | |
|---|---|
| PATENT NO. | : 7,463,362 B2 |
| APPLICATION NO. | : 11/106348 |
| DATED | : December 9, 2008 |
| INVENTOR(S) | : Joseph M. Lasker et al. |

It is certified that error appears in the above-identified patent and that said Letters Patent is hereby corrected as shown below:

In the Title Page of the Letters Patent:

In Column 1, Item 75 - the Inventors, please correct the first name of the last inventor to read as follows:

[Mathew] -- Matthew --

Signed and Sealed this

Tenth Day of February, 2009

JOHN DOLL
*Acting Director of the United States Patent and Trademark Office*